United States Patent [19]

Sandyk

[11] Patent Number: 5,691,324
[45] Date of Patent: *Nov. 25, 1997

[54] METHODS USEFUL FOR THE TREATMENT OF NEUROLOGICAL AND MENTAL DISORDERS RELATED TO DEFICIENT SEROTONIN NEUROTRANSMISSION AND IMPAIRED PINEAL MELATONIN FUNCTIONS

[76] Inventor: Reuven Sandyk, 7 Piper Ct., Roslyn, N.Y. 11576

[*] Notice: The term of this patent shall not extend beyond the expiration date of Pat. No. 5,470,846.

[21] Appl. No.: 437,273

[22] Filed: May 8, 1995

Related U.S. Application Data

[63] Continuation-in-part of Ser. No. 181,677, Jan. 14, 1994, Pat. No. 5,470,846.
[51] Int. Cl.$^6$ .................... A61K 31/60; A61K 31/56; A61K 31/40; A61K 31/21
[52] U.S. Cl. .................. 514/159; 514/160; 514/250; 514/355; 514/345; 514/654; 514/419; 514/657
[58] Field of Search .............................. 514/159, 160, 514/250, 355, 345, 654, 419, 657

[56] References Cited

U.S. PATENT DOCUMENTS 5,470,846  11/1995  Sandyk ........................... 514/159

OTHER PUBLICATIONS

Physicians' Desk Reference, 1989, pp. 625, 1003, 1004, 1701, 1702, 1881.

Physicians' Desk Reference for Nonprescription Drugs, 1991, pp. 584–586.

Merck Index, 1989, p. 1508.

*Primary Examiner*—José G. Dees
*Assistant Examiner*—Mary C. Cebulak
*Attorney, Agent, or Firm*—Graham & James LLP

[57] ABSTRACT

A composition is described which is useful for treating neurological and mental disorders which are associated with and/or related pathogenetically to deficient serotonin neurotransmission and impaired pineal melatonin functions in humans the composition being administered in combination with a sufficient amount of an AC pulsed magnetic field alone or in combination with a sufficient amount of a DC magnetic field to the brain of a human in need of such treatment which composition comprises an effective amount of a composition which increases serotonin transmission to the human to be treated. A method of treating neurological and mental disorders which are associated with and/or related pathogenetically to deficient serotonin transmission and impaired pineal melatonin functions in humans is described which comprises administering to a human in need thereof an effective amount of a composition which increases serotonin transmission to the human to be treated followed by the application to the brain of the human of a sufficient amount of AC pulsed magnetic field of proper intensity and frequency alone or in combination with a sufficient amount of a DC magnetic field of proper intensity and frequency to treat the disorder.

23 Claims, 13 Drawing Sheets

FIG. IA
FIG. IB
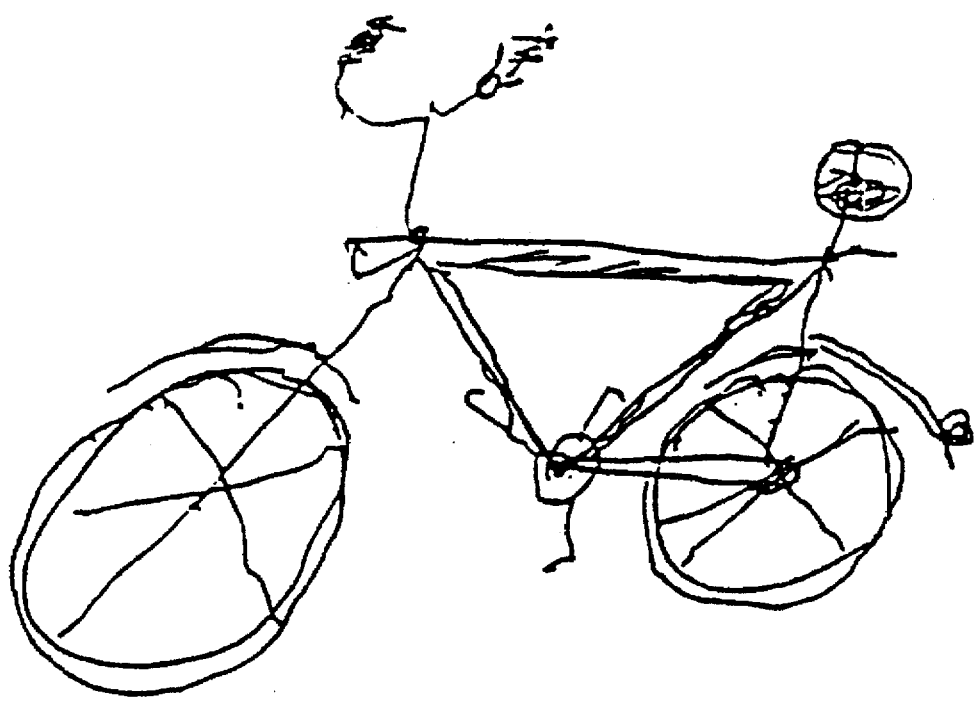

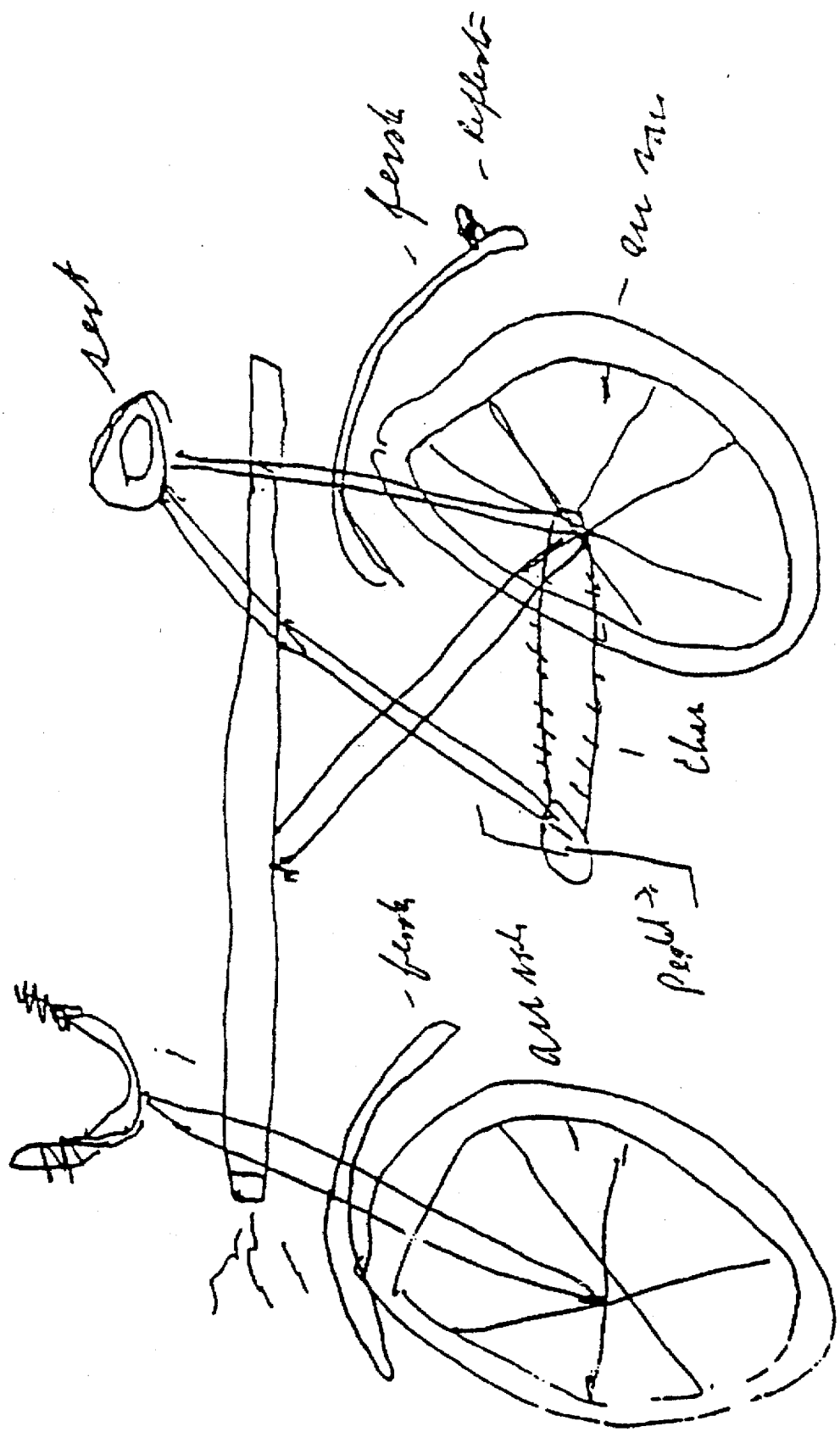
FIG. IC

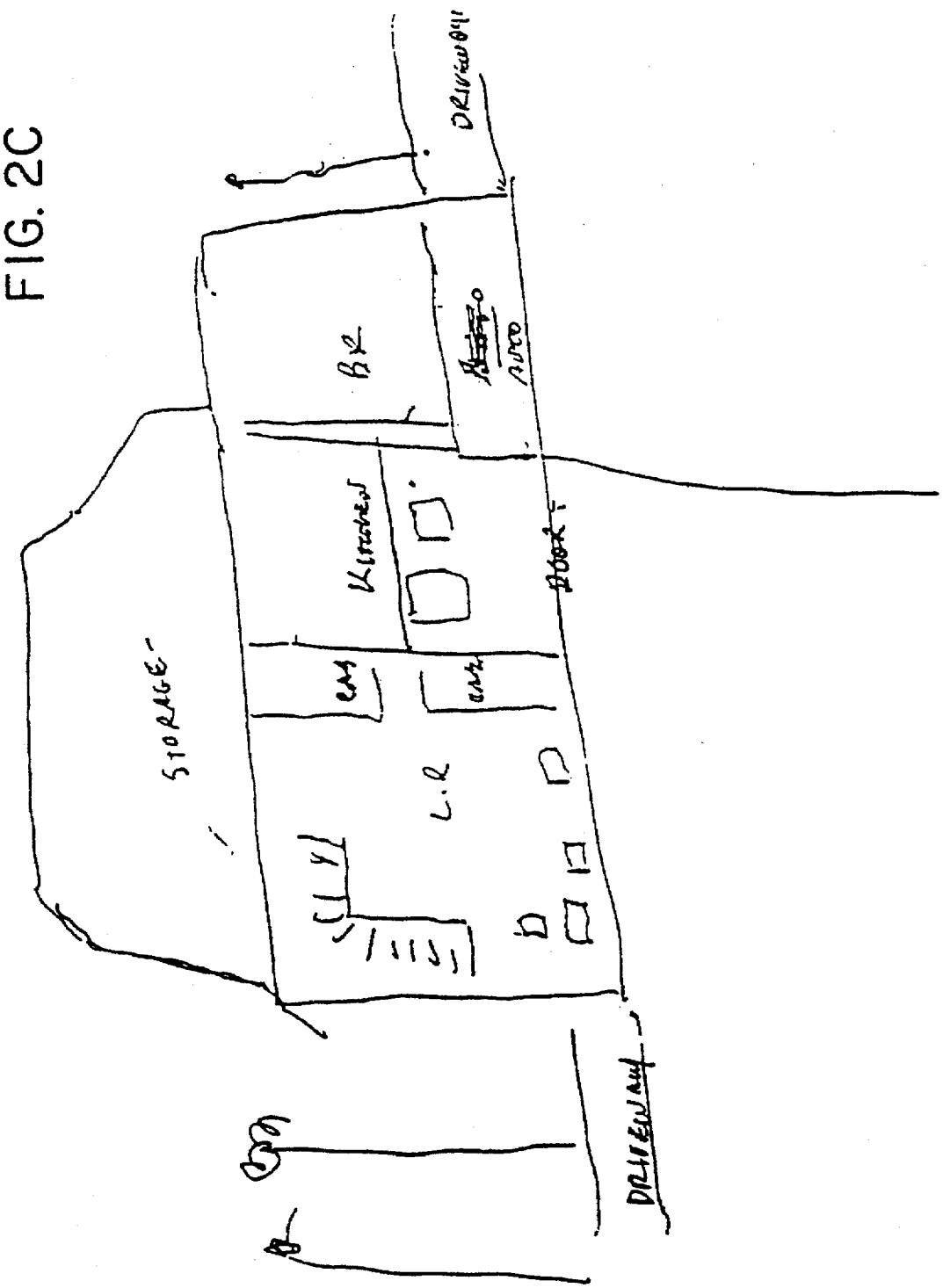

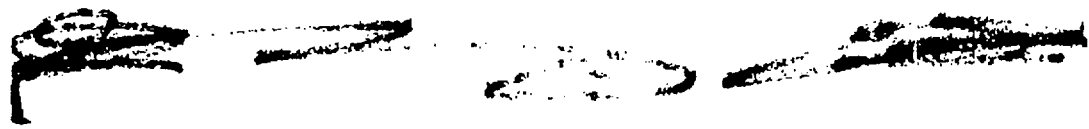
FIG. 4B

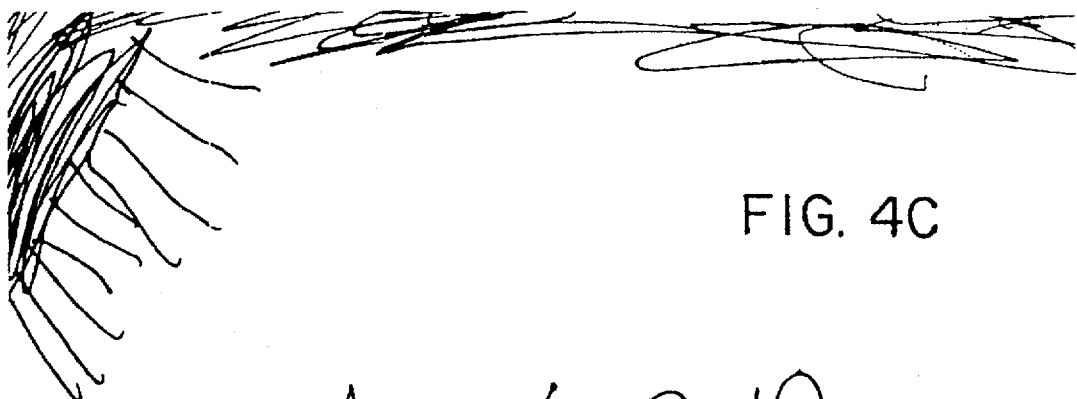
FIG. 4C
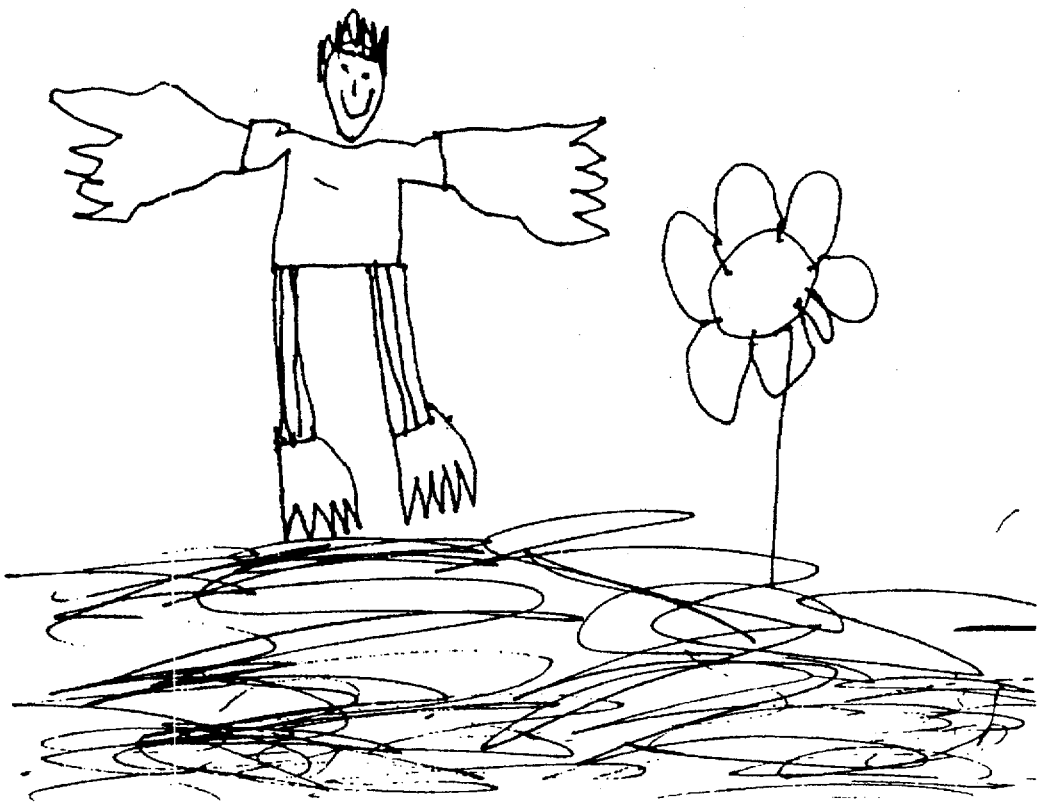

FIG. 5
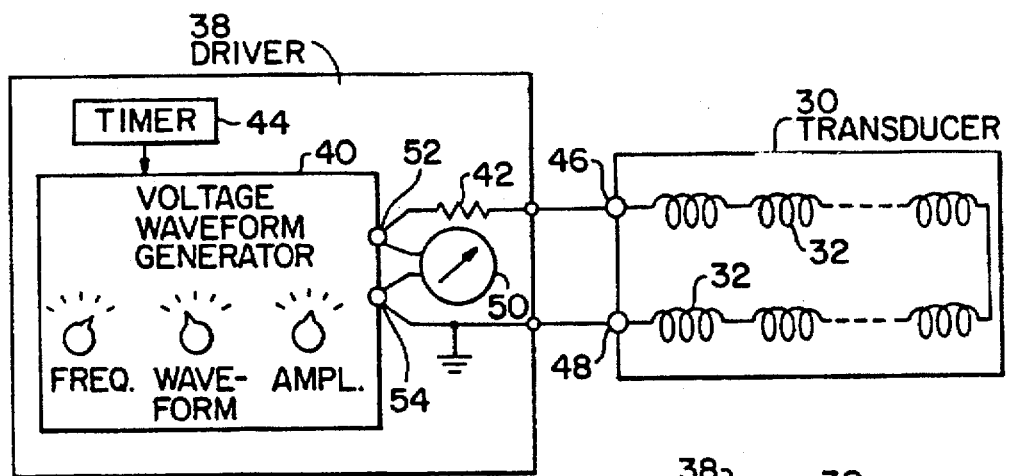
FIG. 6B
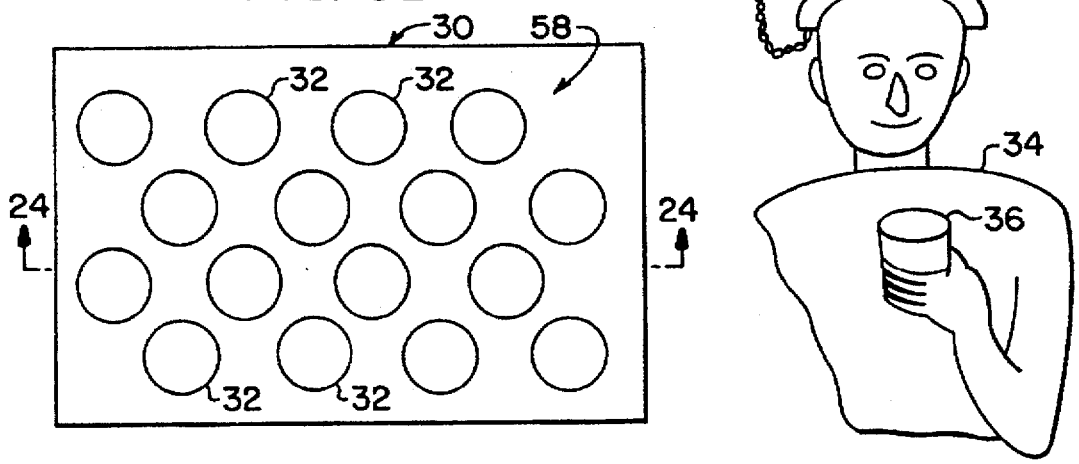
FIG. 8
FIG. 7
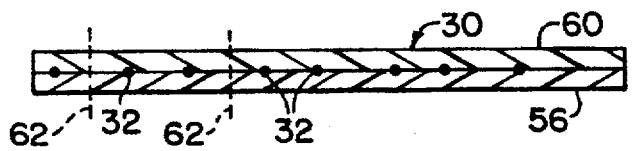
FIG. 6A
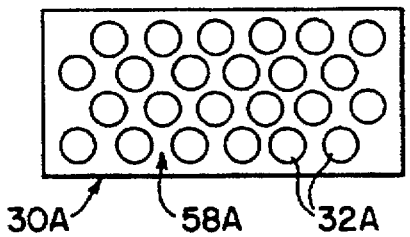

METHODS USEFUL FOR THE TREATMENT OF NEUROLOGICAL AND MENTAL DISORDERS RELATED TO DEFICIENT SEROTONIN NEUROTRANSMISSION AND IMPAIRED PINEAL MELATONIN FUNCTIONS

This is a continuation-in-part of my application Ser. No. 08/181,677 filed Jan. 14, 1994, now U.S. Pat. No. 5,470,846.

BACKGROUND OF THE INVENTION

The present invention relates to compositions for and methods of treating neurological and mental disorders which are associated with and/or related pathogenetically to deficient serotonin neurotransmission and impaired pineal melatonin functions in humans.

The pineal gland is a magnetosensor organ in the brain of humans and other mammals and its stimulation with an AC pulsed magnetic field has shown beneficial effects in the treatment of neurological and mental disorders which are associated with or related pathogenetically to impairment of pineal melatonin functions including multiple sclerosis, Parkinson's disease, dystonia, tardive dyskinesia, epilepsy, migraine, Alzheimer's disease, depression (including seasonal affective disorder), and schizophrenia.

For many years physiologists considered the pineal gland, lodged deep within the brain, a vestigial organ which is merely an anatomical remnant of a primary sensory system. To the clinician the pineal gland, by virtue of its midline position and calcification, was of interest as a radiological landmark to identify intracranial space occupying processes. The pineal gland attracted scientific attention in 1963, when its primary secretion, melatonin, was first recognized as a hormone. Wurtman and Axelrod (1965) "The pineal gland." *Scientific American*, 231, 50–60) termed the pineal gland a "neuroendocrine transducer," an organ which converts neural signals from the external environment such as photic, acoustic, thermic, and magnetic cues into neuroendocrine output which acts on the nervous system largely via the secretion of its principal hormone melatonin. The pineal gland is unique among endocrine organs for a number of reasons: (1) it is one of the few unpaired endocrine organs; (2) on a weight basis, it receives one of the richest blood supplies of any organ; (3) it lies outside the blood brain barrier, but has direct access to the cerebrospinal fluid (CSF) via the third ventricle; (4) it produces and/or contains high concentrations of a number of different indoleamines and low molecular weight peptides of probable endocrine importance; and (5) it is responsive to changes in magnetic field strength and to external electrical stimuli (Foley et al., (1986) "Pineal indoles: significance and measurement." *Neuroscience & Biobehavioral Reviews*, 10, 273–293).

Over the past several years scientists have come to suspect that melatonin is a "master hormone" involved in the control of circadian rhythms (biological cycles that recur at approximately 24-hour intervals), and protecting against some of the common diseases of aging. Melatonin is now recognized to exert an important influence on a host of biological functions including synchronization of biological rhythms, stabilization of neuronal activity, regulation of sexual maturation and reproduction, immunomodulation, temperature control, sleep, mood, pain control, cognitive functions, and motor behavior (Ehrlich and Apuzzo (1985) "The pineal gland: anatomy, physiology, and clinical significance." *Journal of Neurosurgery*, 63, 321–341; Miles and Philbrick (1988) "Melatonin and Psychiatry." *Biological Psychiatry*, 23, 405–425; Romijn (1978). "The pineal, a tranquillizing organ?" *Life Sciences*, 23, 2257–2274; Lakin et al., (1981) "Involvement of the pineal gland and melatonin in murine analgesia." *Life Sciences*, 29, 2543–2551; Kavaliers et al., (1983) "Ageing, opioid analgesia and the pineal gland." *Life Sciences*, 32, 2279–2287; Cotzias et al., (1971) "Melatonin and abnormal movement induced by L-dopa in mice." *Science*, 173, 450–452; Reiter (1991) "Pineal melatonin: cell biology of its synthesis and of its physiological interactions." *Endocrine Reviews*, 12, 151–180).

Many of the biological effects of melatonin result from its action on serotonergic neurons indicating that the neurotransmitter serotonin is an important mediator of melatonin's action (Anton-Tay et al., (1968) "Brain serotonin concentration: elevation following intraperitoneal administration of melatonin." *Science*, 162, 277–278; Gaffori and Van Ree (1985) "Serotonin and antidepressant drugs antagonize melatonin-induced behavioral changes after injection into the nucleus accumbens of rats." *Neuropharmacology*, 24, 237–244; Namboodiri et al., (1983) "5-hydroxytryptophan elevates serum melatonin." *Science*, 221, 659–661; Aldegunde et al., (1985) "Effects of pinealectomy on regional brain serotonin metabolism." *International Journal of Neuroscience*, 26, 9–13; Sugden and Morris (1979) "Changes in regional brain levels of tryptophan, 5-hydroxytryptamine and 5-hydroxyindoleacetic acid, dopamine and noradrenaline after pinealectomy in the rat." *Journal of Neurochemistry*, 32, 1593–1594; Olcese (1985) "Enhancement of melatonin's antigonadal action by daily injections of the serotonin uptake inhibitor fluoxetine in male hamsters." *Journal of Neural Transmission*, 64, 151–161; Smythe and Lazarus (1974) "Growth hormone responses to melatonin in man." *Science*, 184, 1373; Koulu and Lammintausta (1979) "Effect of melatonin on L-tryptophan and apomorphine-stimulated growth hormone secretion in man." *Journal of Clinical Endocrinology & Metabolism*, 49, 70–72).

Melatonin secretion has been shown to change across the lifespan, peaking in childhood and gradually decreasing after puberty. The gradual decline in the secretory activity of the pineal gland after puberty has generally been linked with the process of aging as melatonin is thought to counteract the deleterious effects of oxygen free radicals—unstable molecules thought to play an important part in atherosclerosis and other diseases associated with aging (Nair et al., (1986) "Plasma melatonin—an index of brain aging in humans?" *Biological Psychiatry*, 21, 141–150; Sack et al., (1986) "Human melatonin production decreases with age." *Journal of Pineal Research*, 3, 379–388; Armstrong and Redman (1991) "Melatonin: a chronobiotic with antiaging properties?" *Medical Hypotheses*, 34, 300–309).

Impaired pineal melatonin functions have been implicated in the pathophysiology of numerous systemic, neurological and mental disorders including cancer, autoimmune disorders (i.e., rheumatoid arthritis, systemic lupus), diabetes mellitus, hypercholesterolemia, mental depression including seasonal affective disorder (SAD), and premenstrual syndrome (PMS; late luteal phase dysphoric disorder), schizophrenia, Parkinson's disease, Alzheimer's disease, Korsakoff's dementia, tardive dyskinesia, epilepsy, narcolepsy, migraine, multiple sclerosis, panic disorder, Gilles de la Tourette's syndrome, obsessive compulsive disorder, and anorexia nervosa. These diseases are associated either with deficient melatonin production and/or disruption of circadian melatonin secretion, as disclosed in Anton-Tay et al., (1971) "On the effects of melatonin upon human brain. Its possible therapeutic implications." *Life Sciences*, 10, 841–850; Smith et al., (1978) "Decrease in human serum melatonin concentrations with age." *Journal of Neural Transmission*, 13 (Suppl), 396; Payel et al., (1980) "Vasotocin, melatonin and narcolepsy: possible involvement of the pineal gland in its patho-physiological mechanism." *Peptides*, 1, 281–284; Perry et al., (1990) "Altered wave form of plasma noturnal melatonin secretion in premenstrual depression." *Archives of General Psychiatry*, 47, 1139–1146; Martin et al., (1984) "Decreased 6-hydroxymelatonin excretion in Korsakoff's psychosis." *Neurology*, 34, 966–968; Fanget et al., (1989) "Nocturnal plasma melatonin levels in schizophrenic patients." *Biological Psychiatry*, 25, 499–501; Skene et al., (1990) "Daily variation in the concentration of melatonin and 5-methoxytryptophol in the human pineal gland: effect of age and Alzheimer's disease." *Brain Research*, 528, 170–174; Souetre et al., (1989) "Abnormal melatonin response to 5-methoxpsoralen in dementia." *American Journal of Psychiatry*, 146, 1037–1040; Renfrew et al., (1987) "Circadian rhythms in Alzheimer's disease." *Neurosciences Abstracts*, 1, 322; Armstrong and Redman (1991) "Melatonin: a chronobiotic with antiaging properties?" *Medical Hypotheses*, 34, 300–309; Nair et al., (1986) "Plasma melatonin—an index of brain aging in humans?" *Biological Psychiatry*, 21, 141–150; Tohgi et al., (1992) "Concentrations of serotonin and its related substances in the cerebrospinal fluid in patients with Alzheimer-type dementia." *Neuroscience Letters*, 141, 9–12; Fertl et al., (1991) "Circadian secretion pattern of melatonin in Parkinson's disease." *Journal of Neural Transmission*, 3, 41–47; Fertl et al., (1993) "Circadian secretion pattern of melatonin in de novo Parkinsonian patients: evidence for phase-shifting properties of 1-dopa." *Journal of Neural Transmission* (P-D Sect), 5, 227–234; Sandyk (1992) "The pineal gland and the clinical course of multiple sclerosis." *International Journal of Neuroscience*, 62, 65–74; Sandyk (1992) "The pineal gland and multiple sclerosis." (Editorial) *International Journal of Neuroscience*, 63, 206–215; Sandyk and Awerbuch (1993) "Nocturnal melatonin secretion in multiple sclerosis patients with affective disorders." *International Journal of Neuroscience*, 68, 227–240; Toglia (1986) "Is migraine due to a deficiency of pineal melatonin?" *Italian Journal of Neurological Sciences*, 7, 319–32; Sandyk and Kay (1990) "Pineal melatonin in schizophrenia: a review and hypothesis." *Schizophrenia Bulletin*, 16, 653–662; Sandyk et al., (1990) "Pineal gland calcification and tardive dyskinesia." *Lancet*, 335, 1528; Robinson et al., (1991) "Serum melatonin levels in schizophrenic and schizoaffective hospitalized patients." *Acta Psychiatrica Scandinavica*, 84, 221–224; Miles and Philbrick (1988) "Melatonin and Psychiatry." *Biological Psychiatry*, 23, 405–425; Nir et al., (1969) "Changes in the electrical activity of the brain following pinealectomy." *Neuroendocrinology*, 4, 122–127; Philo (1982) "Catecholamines and pinealectomy-induced convulsions in the gerbil (*Meriones unguiculatus*)." *Progress in Clinical Biological Research*, 92, 233–241; Reiter et al., (1973) "Nature and time course of seizures associated with surgical removal of the pineal gland from parathyroidectomized rats." *Experimental Neurology*, 38, 386–397); McIntyre et al., (1986) "Reduced plasma melatonin in panic disorder." *Biological Psychiatry*, 21, 1438–1439; McIntyre et al., (1990) "Plasma concentrations of melatonin in panic disorder." *American Journal of Psychiatry*, 147, 462–464; Monteleone et al., (1994) "Circadian rhythms of melatonin, cortisol and prolactin in patients with obsessive-compulsive disorder." *Acta Psychiatrica Scandinavica*, 89, 411–415; Catapano et al., (1992) "Melatonin and cortisol secretion in patients with primary obsessive compulsive disorder." *Psychiatry Research*, 44, 217–225; Sandyk and Kay (1991) "Concordance of Tourette's syndrome and bipolar disorder: Possible role of the pineal gland." *International Journal of Neuroscience*, 58, 235–240; Sandyk and Kay (1991) "Pineal melatonin secretion during puberty: possible relevance to Gilles de la Tourette's syndrome." *International Journal of Neuroscience*, 58, 232–235; Molina-Carballo et al., (1994) "Day-night variations in melatonin secretion by the pineal gland during febrile and epileptic convulsions in children." *Psychiatry Research*, 52, 273–283; Waldhauser et al., (1993) "Clinical aspects of the melatonin action: impact of development, aging, and puberty, involvement of melatonin in psychiatric disease and importance of neuroimmunoendocrine interactions." *Experientia;* Brambilla et al. (1988) "Melatonin circadian rhythm in anorexia nervosa and obesity" *Psychiatry Research*, 23, 267–276).

The pineal gland is a neural structure that is functionally related to the visual system. The circadian production of melatonin is determined by the photoperiodic environment to which animals are exposed. Bright light suppresses pineal melatonin synthesis and secretion while ambient darkness stimulates the production and secretion of the hormone. The effects of the environmental illumination on the pineal gland are mediated via a well-delineated retino-hypothalamic-pineal circuit. The rhythms of melatonin secretion are generated by the paired suprachiasmatic nuclei (SCN) of the hypothalamus which serve as the body's biological clock. Serotonin concentrations are higher in the pineal than in any other organ or in any brain region. They exhibit a striking diurnal rhythm, remaining at a maximum level (in the rat) during the daylight hours and falling by more than 80% soon after the onset of darkness, as serotonin is converted to melatonin.

Melatonin is a unique indole derivative. It acts both as a neurotransmitter and neurohormone. Melatonin is lipid soluble and rapidly crosses the blood brain barrier and other tissues. Once released from the pineal gland, which is highly vascularized, it enters both the general circulation and the cerebrospinal fluid (CSF). Melatonin acts on the central and peripheral nervous system as well as on peripheral endocrine target tissues. Laboratory studies have indicated that the primary effect of melatonin is on the neuroendocrine system where it has been shown to influence the activity of the hypothalamic-pituitary-gonadal-thyroid-adrenal axis. In addition, melatonin has been shown to be involved in the regulation of the activity of monoaminergic neurotransmitters including serotonin, dopamine and norepinephrine as well as gamma-aminobutyric acid (GABA) and the opioid peptides as disclosed in (Ehrlich and Apuzzo (1985) "The pineal gland: anatomy, physiology, and clinical significance." *Journal of Neurosurgery*, 63, 321–341; Anton-Tay (1974) "Melatonin: effects on brain function." *Advances in Biochemical Psychopharmacology*, 11, 315–324; Datta and King (1980) "Melatonin: effects on brain and behavior." *Neuroscience & Biobehavioral Reviews*, 4, 451–458; Rosenstein and Cardinali (1986) "Melatonin increases in vivo GABA accumulation in rat hypothalamus, cerebellum, cerebral cortex and pineal gland." *Brain Research*, 398, 403–406; Zisapel et al., (1982) "Inhibition of dopamine release by melatonin: regional distribution in the rat brain." *Brain Research*, 246, 161–163). At a cellular level, melatonin acts to produce antioxidants as by increasing cGMP. It also provides guanine nucleotides for DNA and partakes in DNA repair mechanisms and in maintenance of membranes and other intracellular components (Grad and Rozencwaig (1993) "The role of melatonin and serotonin in aging: update." *Psychoneuroendocrinology,* 18, 283–295).

In addition to the ambient light/dark cycle, the activity of the pineal gland and hence the rate of melatonin secretion is influenced also by the earth's geomagnetic field which is in the order of 30,000–60,000 nanotesla (0.3–0.6 Gauss). The earth's magnetic field is primarily a nontime-varying (DC) field with angle of incidence to the earth's surface increasing with increasing latitude. For comparison, anthropogenic magnetic fields are primarily time varying at 50 or 60 Hz and harmonic of these frequencies. Typical magnetic fields measured in residential settings range from 0.1 microtesla to 3 microtesla at 60 Hz frequency. The geomagnetic field has been a part of the environment throughout the evolution of animals and is used by certain species in their adaptive strategies. Organisms are capable of perceiving its intensity, polarity, and direction (Gould (1984) "Magnetic field sensitivity in animals." *Annual Review of Physiology,* 46, 585–598). It is thought that the circadian rhythmicity of the earth's magnetic field may have an additional "Zeitgeber" (time cue) function in the organization of biological rhythms (Cremer-Bartels et al., (1984) "Magnetic field of the earth as additional zeitgeber for endogenous rhythms?" *Naturwissenschaften,* 71, 567–574; Wever (1968) "Einfluss Schwacher Elektro-magnetischer Felder auf die Circadiane Periodik des Menschen." *Naturwissenschaften,* 55, 29–32).

Since the activity of the pineal gland is sensitive to the influences of the geomagnetic field it has been suggested that it functions as a magnetoreceptor as well (Semm et al., (1980) "Effects of an earth-strength magnetic field on electrical activity of pineal cells." *Nature,* 288, 607–608; Semm (1983) "Neurobiological investigations on the magnetic sensitivity of the pineal gland in rodents and pigeons." *Comparative Biochemistry and Physiology,* 76A, 683–689; Olcese et al., (1988) "Geomagnetic field detection in rodents." *Life Sciences,* 42, 605–613; Demaine and Semm (1985) "The arian pineal gland as an independent magnetic sensor." *Neuroscience Letters,* 62, 119–122; Rudolph et al., (1988) "Static magnetic fields decrease nocturnal pineal cAMP in the rat." *Brain Research,* 446, 159–160). Based on histological studies and electrophysiological single unit recordings from the pineal gland of rodents and pigeons, it has been estimated that 20%–30% of pineal cells respond to magnetic fields (Semm (1983) "Neurobiological investigations on the magnetic sensitivity of the pineal gland in rodents and pigeons." *Comparative Biochemistry and Physiology,* 76A, 683–689). Electrophysiological studies by Reuss et al., (1983) "Different types of magnetically sensitive cells in the rat pineal gland" *Neuroscience Letters,* 40, 23–26 have demonstrated the presence of different types of magnetically sensitive cells in the pineal gland of the rat.

Furthermore, short-term exposure of experimental animals to magnetic fields of various intensities has been shown to alter temporarily the secretion of melatonin while more chronic exposure may even induce ultrastructural morphological changes in the pineal gland (Bardasano et al., (1985) "Ultrastructure of the pineal cells of the homing pigeon *Columba livia* and magnetic fields (first trials)." *Journal Fuer Hirnforschung,* 26, 471–475; Semm et al., (1980) "Effects of an earth-strength magnetic field on electrical activity of pineal cells." *Nature,* 288 607–608; Welker et al., (1983) "Effects of an artificial magnetic field on serotonin N-acetyltransferase activity and melatonin content of the rat pineal gland." *Experimental Brain Research* 50, 426–432; Wilson et al., (1981) "Neuroendocrine mediated effects of electromagnetic field exposure: possible role of the pineal gland." *Life Sciences,* 45, 1319–1332).

The human pineal gland, likewise, is believed to be sensitive to changes in the environmental magnetic fields. Howard et al., (1965) "Psychiatric ward behaviour and geophysical parameters." *Nature,* 205, 1050–1052 made the seminal observations of a relationship between increased geomagnetic activity and the rate of admission of patients to psychiatric facilities. Rajaram and Mitra (1981) "Correlation between convulsive seizure and geomagnetic activity." *Neuroscience Letters,* 24, 187–191 and Venkatraman (1976) "Epilepsy and solar activity. An hypothesis." *Neurology* (India), 24, 1–5 reported an association between changes in the geomagnetic field due to magnetic storms and frequency of seizures in epileptic patients. (Semm (1992) "Pineal function in mammals and birds is altered by earth-strength magnetic fields." In Moore-Ede, Campbell, and Reiter (Eds.), *Electromagnetic Fields and Circadian Rhythmicity,* (pp. 53–62), Birkhauser: Boston) observed in normal subjects placed in the center of a Helmholtz coil system that inversion of the horizontal component of the ambient magnetic field for 30 minutes at midnight resulted in a significant (70%) depression of plasma melatonin concentrations.

Melatonin is a "master hormone" involved in the regulation of a host of physiological functions related to the control of neuroendocrine functions, immunomodulation, analgesia, motor behavior, mood, sleep, cognition, and neurotransmitter synthesis and release (Datta and King (1980) "Melatonin: effects on brain and behavior." *Neuroscience & Biobehavioral Reviews,* 4, 451–458; Ehrlich and Apuzzo (1985) "The pineal gland: anatomy, physiology, and clinical significance." *Journal of Neurosurgery,* 63, 321–341; Frazer and Brown (1987) "Melatonin: a link between the environment and behavior." *Integrative Psychiatry,* 5, 3–26; Bradbury et al., (1985) "Melatonin action in the midbrain can regulate forebrain dopamine function both behaviourally and biochemically." In Brown and Wainwright (Eds.), *The Pineal Gland: Endocrine Aspects* (pp. 327–332) New York: Pergamon Press). Consequently, it is believed that by influencing the activity of the pineal gland and melatonin production and resetting biological rhythms, pulsed magnetic fields may be used therapeutically.

I and others working in this area believe that pulsed magnetic fields in the picotesla range intensity applied externally over the head are beneficial in the treatment of several neurological disorders including epilepsy, Parkinson's disease, dystonia, tardive dyskinesia, migraine, and multiple sclerosis (Anninos et al., (1991) "Magnetic stimulation in the treatment of partial seizures." *International Journal of Neuroscience,* 60, 141–171; Sandyk and Anninos (1992) "Attenuation of epilepsy with application of external magnetic fields: a case report." *International Journal of Neuroscience,* 66, 75–85; Sandyk (1992) "The influence of the pineal gland on migraine and cluster headaches and the effects of treatment with picotesla magnetic fields." *International Journal of Neuroscience,* 67, 145–171; Sandyk (1992) "Weak magnetic fields as a novel therapeutic modality in Parkinson's disease." *International Journal of Neuroscience,* 66, 1–15; Sandyk (1992). "Successful treatment of multiple sclerosis with magnetic fields." *International Journal of Neuroscience,* 66, 237–250; Sandyk and Iacono (1993) "Resolution of longstanding symptoms of multiple sclerosis by application of picotesla range magnetic fields." *International Journal of Neuroscience,* 70, 255–269; Sandyk and Iacono (1993) "Reversal of visual neglect in Parkinson's disease by treatment with picotesla range magnetic fields." *International Journal of Neuroscience,* 73, 93–107); Sandyk (1994) "Parkinsonian micrographia reversed by treatment with weak electromagnetic fields."

*International Journal of Neuroscience*, 81, 83–93; Sandyk (1994) "Improvement in short-term visual memory by weak electromagnetic fields in Parkinson's disease." *International Journal of Neuroscience*, 81, 67–82; Sandyk (1994) "A drug naive Parkinsonian patient successfully treated with weak electromagnetic fields." *International Journal of Neuroscience*, 79, 99–110; Sandyk (1994) "Alzheimer's disease: improvement of visual memory and visuoconstructive performance by treatment with picotesla range magnetic fields." *International Journal of Neuroscience*, 76, 185–225; Sandyk and Dann (1994) "Weak electromagnetic fields attenuate tremor in multiple sclerosis." *International Journal of Neuroscience*, 79, 199–212; Sandyk (1994) "Improvement in word-fluency performance in patients with multiple sclerosis by electromagnetic fields." *International Journal of Neuroscience*, 79, 75–90; Sandyk (1994) "Reversal of visuospatial hemi-inattention in patients with chronic progressive multiple sclerosis by treatment with weak electromagnetic fields." *International Journal of Neuroscience*, 79, 169–184).

However, I believe that the therapeutic efficacy of externally applied magnetic fields, administered as described in the prior art without the use of any pharmacological-nutritional composition, is limited by several factors:

First, the pineal gland tends to undergo calcification with progression of age and particularly in association with various disease states (Trentini et al., (1987) "Pineal calcification in different physiopathological conditions in humans." In Trentini et al., *Fundamentals and clinics in pineal research*, (pp. 291–304), New York: Raven Press; Welsh (1985) "Pineal calcification: structural and functional aspects." *Pineal Research Reviews*, 3, 41–68; Zimmerman and Bilaniuk (1982) "Age-related incidence of pineal calcification detected by computed tomography." *Radiology*, 142, 659–662; Sandyk et al., (1990) "Pineal gland calcification and tardive dyskinesia." *Lancet*, 335, 1528; Sandyk et al., (1991) "Pineal calcification and anticonvulsant responsiveness to artificial magnetic stimulation in epileptic patients." *International Journal of Neuroscience*, 60, 173–175; Sandyk and Awerbuch (1991) "The pineal gland in multiple sclerosis." *International Journal of Neuroscience*, 61, 61–67. For instance, in the case of epileptic patients it has been found that patients who demonstrated calcification of the pineal gland on computed tomography (CT) scan responded less favorably to magnetic treatment in terms of seizure control than those subjects who showed no calcification of the pineal gland (Sandyk et al., (1991) "Pineal calcification and anticonvulsant responsiveness to artificial magnetic stimulation in epileptic patients." *International Journal of Neuroscience*, 60, 173–175).

Second, the secretory activity of the pineal gland, as reflected by nocturnal melatonin plasma levels, diminishes with age. In addition, aging is associated with diminished capacity of the pineal gland to initiate the production of melatonin after sunset (Nair et al., (1986) "Plasma melatonin—an index of brain aging in humans?" *Biological Psychiatry*, 21, 141–150; Sack et al., (1986) "Human melatonin production decreases with age." *Journal of Pineal Research*, 3, 379–388). The decline in the secretory activity of the pineal gland with aging reflects in part the limited regenerative abilities of the pineal cells due to their neuronal derivation.

Finally, melatonin secretion is significantly decreased or its circadian rhythmicity is disrupted in various neurological and mental disorders including multiple sclerosis, Parkinson's disease, Alzheimer's disease, Korsakoff's dementia, depression, and schizophrenia (Martin et al., (1984) "Decreased 6-hydroxymelatonin excretion in Korsakoff's psychosis." *Neurology*, 34, 966–968; Skene et al., (1990) "Daily variation in the concentration of melatonin and 5-methoxytryptophol in the human pineal gland: effect of aging and Alzheimer's disease." *Brain Research*, 528, 170–174; Nair et al. (1986) "Plasma melatonin rhythm in normal aging and Alzheimer's disease." *Journal of Neural Transmission*, 21 (suppl), 494; Sandyk and Awerbuch (1992) "Nocturnal melatonin secretion in multiple sclerosis patients with affective disorders." *International Journal of Neuroscience*, 68, 227–240; Miles and Philbrick (1988) "Melatonin and psychiatry." *Biological Psychiatry*, 23, 405–425; Fertl et al., (1993) "Circadian secretion pattern of melatonin in de novo Parkinsonian patients: evidence for phase-shifting properties of 1-dopa." *Journal of Neural Transmission*, {P-D Sect}, 5, 227–234).

It is believed that reduction in the activity of the pineal gland in these neurological and mental disorders may be related to various factors including, among others, decrease in pineal receptor sensitivity and/or density, decline in the availability of nutritional co-factors for serotonin and subsequent melatonin synthesis, decline in the capacity of pineal cells to synthesize serotonin from tryptophan, decrease in sympathetic nervous system activity which provides a stimulus for melatonin synthesis, and progressive loss of neurons in the suprachiasmatic nucleus of the hypothalamus which activate the pineal gland.

Thus, a definite need exists in therapy today for an effective treatment for patients with neurological and mental disorders which are associated with and/or related pathogenetically to deficient serotonin neurotransmission and impaired pineal melatonin functions.

SUMMARY OF THE INVENTION

The present invention comprises a composition useful for treating neurological and mental disorders which are associated with and/or related pathogenetically to deficient serotonin neurotransmission and impaired pineal melatonin functions in humans the composition being administered in combination with the application of a sufficient amount of an AC pulsed magnetic field alone or in combination with a sufficient amount of a DC magnetic field to the brain of a human in need of such treatment which composition comprises an effective amount of a composition which increases serotonin transmission to the human to be treated. The present invention also includes a method of treating neurological and mental disorders which are associated with and/or related pathogenetically to deficient serotonin transmission and impaired pineal melatonin functions in humans which comprises administering to a human in need thereof an effective amount of a composition which increases serotonin transmission to the human to be treated followed by the application to the brain of the human of a sufficient amount of an AC pulsed magnetic field of proper intensity and frequency alone or in combination with a sufficient amount of a DC magnetic field of proper intensity and frequency to treat the disorder. I have found that the treatment of Parkinson's disease is particularly effective when a combination of an AC pulsed magnetic field and a DC (direct current) magnetic field is applied simultaneously to the patient's brain.

The present invention thus represents a substantial advance in the treatment of such medical conditions as multiple sclerosis, Parkinson's disease, dystonia, tardive dyskinesia, epilepsy, migraine, Alzheimer's disease, depression, schizophrenia, Gilles de la Tourette's syndrome, Attention Deficit-Hyperactivity Disorder, anxiety and panic disorder, narcolepsy-cataplexy, obsessive compulsive disorder, akathisia and restless legs syndrome, myoclonus and chronic pain syndromes.

The administration of the composition prior to application of the AC pulsed magnetic field is designed to increase serotonin neurotransmission as well as sensitize the pineal gland to a periodic exposure of AC pulsed magnetic fields.

Thus, while AC pulsed magnetic stimulation has been used therapeutically in the past, I have observed in practice that when the composition of the present invention is administered prior to the application of the AC pulsed magnetic field, the patient's clinical response to the pulsed magnetic stimulation is markedly improved.

According to one embodiment of the present invention, the AC pulsed magnetic field is applied in two applications, an initial application is applied to the brain of the patient followed by an interval of time and then a second AC pulse is applied.

When treating patients with Parkinson's disease I have achieved best results in terms of alleviation of tremor, bradykinesia (slowness of movement) and muscular rigidity by simultaneously applying an AC pulsed magnetic field and a DC magnetic field. Preferably, both AC and DC components are applied and, following an interval of time, a second application also comprising both components is applied.

According to a preferred embodiment of the present invention, the composition which is administered prior to the application of the AC pulsed magnetic field, comprises an effective amount of a serotonin precursor, an effective amount of a stimulant to increase plasma tryptophan concentrations, a sufficient amount of a stimulant to facilitate the transport of tryptophan into the brain of the human, an effective amount of a stimulant of serotonin synthesis, an effective amount of a serotonin reuptake inhibitor, an effective amount of a stimulant of serotonin release and an effective amount of a stimulant of serotonin receptors. I have found particularly good results are obtained by additionally increasing brain serotonin concentrations. I achieve this by having my patients increase their intake of the amino-acid tryptophan in their diet 4–8 weeks prior to the application of the magnetic field by consuming foods that are rich in tryptophan such as turkey (preferably 4 ounces twice a week), milk (preferably 8 ounces per day of whole, low-fat, or skim), bananas (preferably 1 per day), nuts (preferably 1–2 ounces per day), and dry-roasted sunflower seeds (preferably 3–4 ounces per day). This nutritional regimen is recommended particularly for patients with multiple sclerosis, depression, obsessive compulsive disorder, anxiety and panic disorder, Gilles de la Tourette's syndrome, Alzheimer's disease and for the management of pain syndromes.

According to a further embodiment of the present invention, the serotonin precursor is L-tryptophan (L-TP) or L-5-hydroxytryptophan (L-5-HTP). L-TP or L-5-HTP may be combined with cofactors for serotonin synthesis such as vitamin $B_1$ (thiamine), vitamin $B_3$ (nicotinic acid), vitamin $B_6$ (pyridoxine) and vitamin C (ascorbic acid) as well as folic acid, biotin, and S-adenosylmethionine. Since serotonin present in the bloodstream is excluded by the blood-brain barrier from entry into the brain, the administration of precursors such as L-TP or L-5-HTP is used to increase brain concentrations of serotonin (Wurtman and Fernstrom (1975) "Control of brain monoamine synthesis by diet and plasma amino acids." *The American Journal of Clinical Nutrition*, 28, 638–647).

According to a further embodiment of the present invention, the stimulant to increase plasma tryptophan concentrations is a salicylate. L-tryptophan is usually transported in the blood in a bound or complexed form with the protein albumin, a plasma component. It has been shown that various salicylates displace tryptophan from its protein binding site with albumin in blood plasma thereby raising the free or unbound tryptophan concentration in the blood. The bond-breaking effect exerted by salicylates on the binding of tryptophan to albumin causes a greater availability of free tryptophan molecules for diffusion into the brain (Tagliamonte et al., (1973) "Increase of brain tryptophan and stimulation of serotonin synthesis by salicylate." *Journal of Neurochemistry*, 20, 909–912). While aspirin is the salicylate preferred, any other pharmaceutically acceptable salicylate such as sodium salicylate would serve as well.

According to a further embodiment of the present invention, the stimulant to facilitate the transport of tryptophan into the brain is preferably vitamin $B_3$, chromium (preferably chromium picolinate) or a mixture thereof. Chromium is an essential cofactor to insulin production and action (Rabinowitz et al., (1983) "Effects of chromium and yeast supplements on carbohydrate and lipid metabolism in diabetic men." *Diabetes Care*, 6, 319–327). Insulin, in turn, facilitates the entry of tryptophan into the brain by inhibiting the uptake of the branched chain amino-acids leucine, isoleucine, and valine which compete with tryptophan for entry into the brain (Wurtman and Fernstrom (1976) "Control of brain neurotransmitter synthesis by precursor availability and nutritional state." *Biochemical Pharmacology*, 25, 1691–1696).

According to a further embodiment of the present invention, the stimulant of serotonin synthesis is preferably vitamin $B_1$, vitamin $B_3$, vitamin $B_6$, biotin, S-adenosylmethionine, folic acid, ascorbic acid, magnesium, coenzyme $Q_{10}$, piracetam or mixtures of two or more thereof.

According to a further embodiment of the present invention, the serotonin reuptake inhibitor is sertraline, nefazodone, trazodone or a mixture thereof. According to a further embodiment of the present invention, the stimulant of serotonin release is preferably fenfluramine (Fuller (1986) "Pharmacologic modification of serotonergic functions: drugs for the study and treatment of psychiatric and other disorders." *Journal of Clinical Psychiatry*, 47 (suppl 4), 4–8).

According to a further embodiment of the present invention, the stimulant of serotonin receptors is preferably ergoloid mesylate (Hydergine®), pergolide mesylate or buspirone. Hydergine® has been shown to improve mental alertness and memory functions in normal subjects and those with organic mental deterioration an effect which is related partly to its stimulating properties of serotonin receptors in the brainstem reticular formation (Depoortere et al., (1975) "Neuropharmacological studies on Hydergine." *Triangle*, 14, 73–79). Ergot derivatives stimulate central dopamine receptors and are employed for the treatment of Parkinson's disease. However, these agents also exhibit serotonin receptor stimulating properties (Markstein (1981) "Neurochemical effects of some ergot derivatives: a basis for their antiparkinson actions." *Journal of Neural Transmission*, 51, 39–59). Buspirone (Buspar®) is a nonbenzodiazepine arixiolytic agent which acts as an agonist at the serotonin (5-HT)$_{1A}$ receptor sites. It behaves as a full agonist at the 5-HT$_{1A}$ cell-body autoreceptor and as a partial agonist at post-synaptic 5-HT$_{1A}$ receptor sites (Cowen (1991) "Serotonin receptor sybtypes: implications for psychopharmacology." *British Journal of Psychiatry*, 159 (suppl. 12), 7–14); Eison and Temple (1986) "Buspirone: review of its pharmacology and current perspectives on its mechanism of action." *The American Journal of Medicine*, 80 (suppl. 3B), 1–9).

It is preferred that the intensity of the magnetic field be in the range of 7.5–75 picotesla. It has been found most beneficial that the duration of the first AC pulse be 15–20 minutes. The magnetic field is a time varying field with a wave form which is sinusoidal, triangular, trapezoidal, square or a composite thereof, dependent upon the condition to be treated.

It is particularly preferred that the two AC magnetic field pulses be applied following administration of the composition of the present invention. It is preferred that the duration of the first AC pulse be in the range of 15–20 minutes and the duration of the second AC pulse be in the range of 15–45 minutes. The AC frequency of each pulse will vary with the condition to be treated. In the case of multiple sclerosis, the AC frequency should be 2 Hz–5 Hz. The AC and DC frequency for the treatment of Parkinson's disease and the AC frequency for the treatment of Alzheimer's disease, migraine, dystonia, tardive dyskinesia, depression and schizophrenia are preferably 5 Hz or higher, preferably 5 Hz–8 Hz. For the treatment of seizure disorders, it is preferred that the AC frequency of the first pulse be in the range of 4–5 Hz and the frequency for the second AC pulse be in the range of 5–7 Hz.

It is preferred that the patient's eyes be shielded during the application of the AC pulsed magnetic fields.

It has also been found to be most effective when administration of the composition of the present invention begins 4–8 weeks, particularly 6–8 weeks, prior to the application of the first AC pulsed magnetic field by administration of the elements of the composition of the present invention.

For the treatment of Gilles de la Tourette's syndrome, the preferred AC frequency is 2 Hz–7 Hz.

For the treatment of Attention Deficit-Hyperactivity Disorder, the preferred AC frequency is 2 Hz–7 Hz.

For the treatment of anxiety and panic disorder, the preferred AC frequency is 5 Hz–7 Hz.

For the treatment of narcolepsy-cataplexy, the preferred AC frequency is 2 Hz–7 Hz.

For the treatment of obsessive compulsive disorder, the preferred AC frequency is 5 Hz–8 Hz.

For the treatment of akathisia and restless legs syndrome, the preferred AC frequency is 5 Hz–8 Hz.

For the treatment of myoclonus, the preferred AC frequency is 2 Hz–7 Hz.

For the treatment of chronic pain syndromes, the preferred AC frequency is 5 Hz–8 Hz.

It is preferred that the AC pulsed magnetic field starts with a given direction and then reverses direction during each cycle. The fields are conveniently applied to the patient's head using a helmet-like transducer array. The fields preferably have lines of force normal to the array. The helmet-like transducer array preferably comprises an array of coils comprising four rows of four coils. Alternatively, the helmet-like transducer array may comprise an array of coils comprising four rows of six coils. Preferably, the helmet-like transducer array comprises an array of coils which are flat i.e. two dimensional or helical i.e. three dimensional.

BRIEF DESCRIPTION OF THE DRAWINGS

FIGS. 1A–C show test results of a patient afflicted with Parkinson's disease treated with an AC pulsed magnetic field without the prior administration of the composition of the present invention. The test is a sequence of drawing assignments, in this case the drawing of a bicycle, wherein FIG. 1A shows the results of the drawing test prior to the application of magnetic treatment, FIG. 1B shows the results of the drawing obtained five minutes after a single AC pulsed magnetic treatment, and FIG. 1C shows the drawing results obtained following 30 minutes of magnetic treatment wherein a second AC pulse has been administered after a 15 minute interval;

FIGS. 2A–C show attempts at drawing by a patient afflicted with Alzheimer's disease wherein FIG. 2A shows an attempted drawing of a house prior to magnetic treatment, FIG. 2B shows an attempted drawing of the house by the patient after two fifteen minute AC pulses of magnetic treatment, and FIG. 2C shows a drawing produced by the patient after treatment according to the present invention which comprised administration of the composition of the present invention followed by the application of two fifteen minute AC pulses of magnetic fields according to the present invention;

FIGS. 3A–D show the drawings by a patient afflicted with schizophrenia wherein FIG. 3A shows the patient's drawing of a house prior to magnetic treatment, FIG. 3B shows the patient's drawing of a house after administration of a placebo magnetic treatment, FIG. 3C shows an attempt by the patient to draw the house after a treatment with two AC magnetic pulses, FIG. 3D shows the patient's drawing (on a reduced scale) after treatment according to the present invention;

FIGS. 4A–C show attempts at a drawing by a 6½ year old child afflicted with Gilles de la Tourette's syndrome wherein FIG. 4A shows an attempted drawing of the human figure prior to magnetic treatment which showed distortions, lack of perspectives and details, and abnormal presentation of the hands each having three projections for fingers. FIG. 4B shows the child's drawing of the human figure after two 15 minute AC pulses of magnetic treatment, and FIG. 4C shows the child's drawing after treatment according to the present invention which comprised administration of the composition of the present invention followed by the application of two fifteen minute AC pulses of magnetic fields according to the present invention.

FIG. 5 is a schematic diagram showing connections of a signal generator to an array of coils for applying AC pulsed magnetic fields to a patient's head;

FIGS. 6A and 6B show plan views of alternate configurations of the array of coils;

FIG. 7 is a sectional view of the array of coils taken along the line 24—24 in FIG. 5;

FIG. 8 is a stylized view showing emplacement of the array of coils upon a patient's head for applying the magnetic fields to the patient's head;

DETAILED DESCRIPTION

Figure 2A:
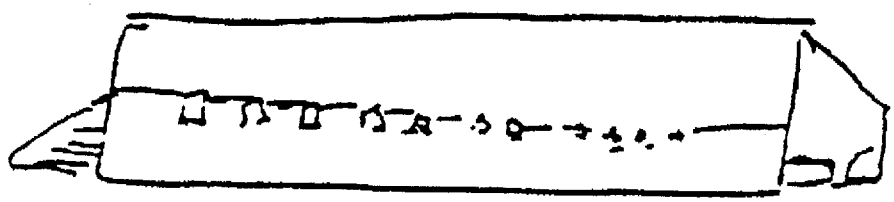

The treatment of the present invention has been found to be most effective when the patient is given the elements of my composition beginning 4–8 weeks, preferably 6–8 weeks, prior to the application of the AC pulsed magnetic field which is preferably applied in two treatments. The composition can comprise one or more of the specific components described above. Particular components can or should be omitted using sound medical judgment including patient contraindications or lack of compatibility with other medication(s) the patient is taking.

In the initial treatment phase, the patient is given a serotonin reuptake inhibitor drug to increase the brain's concentrations of serotonin. The uptake of serotonin back into the nerve terminal inactivates the neurotransmitter after it has been released into the synaptic cleft. Therefore, serotonin reuptake inhibitors enhance serotonergic neurotransmission by increasing the synaptic concentrations of the neurotransmitter thus permitting serotonin to act for a longer period on the postsynaptic receptor. For this purpose, it is preferred to use one of the selective serotonin reuptake inhibitors (e.g., fluoxetine, fluvoxamine, clomipramine, citalopram, paroxetine, sertraline, venlafaxine, nefazodone), preferentially sertraline (Zoloft®; 25–2000 mg., orally per day) taken in the morning with breakfast or nefazodone (Serzone®; 50–600 mg., orally per day).

A second serotonin transmission enhancing drug is given at nighttime. I prefer the drug trazodone (Desyrel®) (25–100 mg., orally). This drug increases serotonergic neurotransmission by inhibiting the reuptake of serotonin in the synaptic cleft and also acts as a serotonomimetic substance through its major metabolite m-chlorophenylpiperazine (m-CCP), a direct and potent postsynaptic serotonin$_{1B}$ receptor agonist.

Clinical experience has shown that administration of these serotonergic drugs for at least four weeks prior to the initiation of AC pulsed magnetic treatment is one of the key components of my pharmacological composition.

On the night prior to application of the magnetic fields the patient is given a serotonin precursor to augment the synthesis of serotonin and melatonin. For this purpose I prefer to use a preparation containing the essential amino-acid tryptophan (L-tryptophan, 500 mg –3 g, orally) or a preparation containing L-5-hydroxytryptophan (L-5-HTP) (100–200 mg., orally) taken at bedtime. L-5-HTP produces more pronounced elevations of brain serotonin levels and of pineal melatonin content than L-tryptophan and is therefore preferred.

One to two hours prior to application of magnetic treatment the patient is given:

(a) a preparation containing the serotonin precursor L-tryptophan (500–1000 mg., orally) or L-5-HTP (100–200 mg., orally). In my experience, L-5-HTP is the agent of choice;

(b) a drug which stimulates the release of serotonin from serotonergic neurons. For this purpose I prefer to use the drug fenfluramine hydrochloride (Pondimin®; 10–50 mg., orally); and (c) a drug which stimulates serotonin receptors from the class of ergot derivatives (e.g., bromocriptine, lisuride, pergolide and mesulergine). I prefer to use the drug pergolide mesylate (Permax®, 0.025–0.05 mg., orally). Alternatively, buspirone (Buspar®, 2.5–7.5 mg., orally) can be used to stimulate serotonin receptors. These drugs are used as part of the composition exclusively in patients with multiple sclerosis.

In my experience, the administration of a serotonin precursor alone or combined with a serotonin releasing agent and an ergot derivative or buspirone (in the case of multiple sclerosis) one to two hours preceding the application of magnetic treatment is highly important for the success of the procedure; not only is the effect of magnetic treatment more pronounced, but the duration of the clinical response to the procedure is significantly longer when the patient receives my composition prior to application of the magnetic field.

The procedure continues with application of an AC pulsed magnetic field at an oscillatory frequency dependent on the specific neurological or mental disease being treated. Magnetic fields are applied over the scalp in a pulsed exposure (i.e., "on/off"). This method was chosen as several experimental studies have demonstrated that intermittent exposure to magnetic fields is biologically more effective than static or continuous wave sinusoidal exposure (Wilson et al., (1992) "Effects of electromagnetic field exposure on neuroendocrine function." In Moore-Ede et al., *Electromagnetic fields and circadian rhythmicity* (pp. 29–50), Birkhauser: Boston). Magnetic treatment is applied during the day, but preferentially at nighttime (at least 2 hours after sunset) since nighttime exposure has been shown in experimental animals to induce greater melatonin response to magnetic fields than daytime exposure (Welker et al., (1983) "Effects of an artificial magnetic field on serotonin Nacetyltransferase activity and melatonin content of the rat pineal gland." *Experimental Brain Research*, 50, 426–432). Magnetic fields are applied in a quiet and magnetically unshielded room with the patient's eyes covered with eye shields to prevent exposure to light thus maximizing pineal stimulation. Magnetic fields are applied about 1–2 minutes after shielding of the patient's eyes. This period is chosen since it has been shown that melatonin secretion is increased within one minute after exposure of a subject to a dark environment. During the interval between magnetic treatments the patient may remove the eye shields.

The first magnetic pulse is given for a period of 15–20 minutes using an AC frequency of 2 Hz–5 Hz. The optimum frequency varies with the specific disease being treated. In my experience, this is the time which is usually required until one can observe that the patient's face becomes pale. After a break of 15–45 minutes, during which time the patient's facial color has returned to normal, a second magnetic pulse is applied for a period of 15–45 minutes using a higher AC frequency of 5 Hz–8 Hz. During this period the patient's face becomes pale once again usually more intensively than after application of the first magnetic pulse. According to my experience, the application of the second AC pulse is extremely beneficial as it produces a more profound clinical effect. In addition, application of a second AC pulse is also associated with a greater degree of facial pallor. It is of note that facial pallor is usually more prominent in patients who have received my composition prior to the application of the magnetic fields.

Evidence of the success of the treatment of the present invention is demonstrated by improvement in motor, sensory and autonomic functions as well as behavioral and intellectual skills, sleep, mood and level of energy. For example, in the case of patients having multiple sclerosis, including those with a chronic progressive course of the disease, noticeable improvements in vision, bladder control, balance, motor coordination, sensory symptoms, lessened fatigue, as well as mood, sleep and cognitive functions have been observed. In the laboratory, there was objective documentation that this treatment of the present invention was associated with electrophysiological changes in the recordings of the visual and auditory brainstem evoked potential amplitudes and latencies. In the case of patients having Parkinson's disease, noticeable improvements were observed with respect to attenuation of resting tremor and muscular rigidity, mobility and posture were improved, mood elevated, and cognitive functions particularly short-term memory and visuospatial functions were improved. The treatment according to the present invention has provided objective evidence of effectiveness as evidenced by reduction in tremor and improved visuospatial functions on drawing tasks and normalization of electroencephalographic brain wave activity.

In the case of patients having Gilles de la Tourette's syndrome, I have observed attenuation of motor and vocal tics, reduction in echolalia and coprolalia, attenuation of obsessive-compulsive behavior such as compulsive touching, diminished hyperactive and destructive behavior, diminished level of frustration, improved attention span and concentration, reversal of learning disabilities including dyslexia, improved cognitive functions such as short-term memory, visuospatial functions, word finding, writing, and arithmetic, improvement of sleep with resolution of night terrors and somnambulism. Moreover, changes in hormonal and peptide levels with plasma levels of prolactin and growth hormone as well as beta-endorphin returning to normal can be objectively measured.

In the case of patients having anxiety and panic disorder, I have observed reduction in anxiety level, mental relaxation, improved ability to tolerate stressful situations, improvement in mood and sleep, resolution of panic attacks including their autonomic symptoms such as palpitations, tachycardia, hyperventilation, excessive sweating, headache and weakness in the extremities. In the case of patients having idiopathic narcolepsy-cataplexy syndrome and in patients manifesting narcolepsy-cataplexy secondary to other diseases such as multiple sclerosis or the Klein-Levin syndrome, I have observed dramatic reduction in daytime sleepiness, increased daytime level of energy, and reduction in the frequency of cataplectic attacks.

In the case of patients having obsessive compulsive disorder (OCD) or those manifesting obsessive compulsive behavior secondary to other diseases such as Gilles de la Tourette's syndrome, Parkinson's disease and multiple sclerosis, I have observed reduction in the occurrence of intrusive thoughts, attenuation of irrational impulses to some form of action (e.g., compulsive touching and shouting obscenities in patients with Tourette's syndrome; compulsive grooming in patients with idiopathic OCD), diminished level of anxiety, and improvement in mood. In the case of patients having akathisia and restless legs syndrome either as an idiopathic manifestation or secondary to other diseases such as Parkinson's disease, schizophrenia and renal failure, I have observed a dramatic reduction in symptoms with patients experiencing the infrequent occurrence of paresthesias in the limbs particularly in the calves with diminished urge to move the limbs to obtain relief particularly at night, improvement in sleep, and reduction in associated mental symptoms such as anxiety and depression.

In the case of patients having myoclonus (i.e., a neuromuscular disorder characterized by the occurrence of irregular, asynergic, and jactitious contractions of muscles producing nonrepetitive, brief, involuntary movements in various body areas) as a symptom of epilepsy, neurodegenerative disease such as Parkinson's disease, multiple sclerosis or amyotrophic lateral sclerosis (ALS) and Tourette's syndrome, I have observed attenuation in the frequency and severity of these muscular contractions which was associated with improvement in other symptoms of the underlying neurological disorder. In the case of patients having pain syndromes (e.g., pain associated with peripheral neuropathy, nerve root compression and trigeminal neuralgia, migraine headaches, myalgia and pain syndromes of multiple sclerosis) I have observed marked analgesic effects in response to the application of pulsed magnetic fields in conjunction with the pharmacological composition.

Once the composition has been administered, the AC pulsed magnetic fields are subsequently applied preferably via an external magnetic coil assembly, or transducer. The transducer is constructed of flexible substrate which allows the transducer to be bent and positioned on the head of a patient in the form of a helmet. The transducer is constructed of a set of coils positioned side-by-side in a two-dimensional array. In the preferred embodiment of the invention, the transducer is constructed of 16 coils arranged in a matrix of four rows by four columns, and the area of each coil is preferably 3.14 $cm^2$. When these coils are carrying an electric current, they produce magnetic fields with lines of force parallel to the axes of the respective coils. The locations of the coils are such that the resultant magnetic fields are uniform. The produced magnetic fields are alternating and can be in the frequency range of 1 Hz to 10 KHz, and their intensity can be less than approximately 60 microtesla. For clinical purposes herein, it is preferred to employ magnetic fields strength in the range of 7.5–75 picotesla with an AC frequency in the range of 2 Hz–8 Hz, the optimum frequency depending on the specific disease. In the experience of the inventor higher amplitudes of the exposed magnetic fields above 75 picotesla and up to 1000 picotesla do not provide additional clinical benefit.

To maintain the effects of the treatment, "maintenance therapy" is implemented during which time the procedure may be repeated once to three times every week depending on the patient's clinical needs. During the period of "maintenance therapy" the patient continues treatment with all the elements of the composition except for those which are given the night before (i.e., L-tryptophan or L-5-HTP) and just prior to the application of magnetic treatment (L-tryptophan or L-5-HTP, fenfluramine, and pergolide mesylate). During the entire treatment period as well as the "maintenance therapy" period the patient continues to receive the usual medications for the disease. For instance, in the case of Parkinson's disease, the patient continues to use his antiParkinsonian medications while receiving the composition and the magnetic treatment. In some instances, antiParkinsonian medications may be reduced during the period of magnetic treatment or "maintenance therapy" based on the judgment of the doctor.

A further benefit of the present invention has been found in that the effects of the pulsed magnetic treatment may be enhanced by applying the magnetic fields in conjunction with a specific AC frequency for each disease state. It is noteworthy that the clinical response to magnetic fields is not influenced significantly by the amplitude of the magnetic fields as long as the intensity of stimulation is in the picotesla range. Specifically, no apparent difference in the clinical response of these patients is noted when the strength of the magnetic fields applied ranges from 7.5 picotesla to 75 picotesla (i.e., ten-fold increase in the amplitude did not impact on the clinical response).

It has been observed that patients with multiple sclerosis experience the greatest degree of improvement of symptoms when administered magnetic fields of an AC frequency in the range of 2 Hz–5 Hz. Patients with chronic progressive multiple sclerosis require an AC frequency of 2 Hz–4.5 Hz. With higher frequencies, patients may even experience worsening of symptoms.

On the other hand, patients with Parkinson's disease usually require a higher combined AC/DC pulsed magnetic field frequency of stimulation. The best clinical response has been obtained using the range of 5 Hz–8 Hz. Patients with Alzheimer's disease usually require a similar range of frequencies, namely 5 Hz–8 Hz, to achieve the most favorable clinical response. Likewise, patients with dystonia, tardive dyskinesia, migraine, depression, and schizophrenia require a frequency of stimulation in the range of 5 Hz–8 Hz. Patients with seizure disorders require an AC frequency in the range of 4 Hz–7 Hz.

In summary, therefore, it appears that the AC frequency of the applied magnetic fields is more critical to the clinical response to magnetic treatment than the intensity of the magnetic fields. It is possible that the pineal gland is differently affected in these neurological and mental disorders requiring a different AC frequency of stimulation in each of these disorders.

With reference to FIGS. 5–8, there is shown a transducer 30 which is employed in the practice of the invention to impress magnetic fields upon the brain of a patient. The transducer 30 comprises a set of coils 32, and is placed on the head of a patient 34. Upon energization of the coils 32 with electric current, the coils 32 produce magnetic fields which are directed into the brain, and particularly into the area of the pineal gland, of the patient 34. The patient 34 holds a cup 36 to demonstrate the inventive feature of ingesting various pharmacological and nutritional components of the composition prior to application of the magnetic fields. Electric current is applied to the coils 32 by a driver 38, the driver 38 including a voltage generator 40 and an output resistor 42 by which the generator 40 is coupled to the coils 32. Also included in the driver 38 is a timer 44 for activating the generator 40 to provide a sequence of pulses of output voltage which are applied to the resistor 42. The resistor 42 has a resistance of approximately 0.5 megohm in the preferred embodiment of the invention, and the coils 32 are connected in series to provide a total resistance of approximately one ohm between the terminals 46 and 48 of the transducer 30. A volt meter 50 is connected between output terminals 52 and 54 of the generator 40 to provide an indication of the magnitude of the output voltage of the generator 40.

The coils 32 and the resistor 42 constitute a series circuit between the terminals 52 and 54 of the generator 40. Since the internal impedance of the driver 38, as provided by the resistor 42, is several orders of magnitude greater than that of the transducer 30, the voltage generator 40 in combination with the resistor 42 acts as a current source to provide a current to the transducer 30 proportional to the voltage outputted by the generator 40. In view of the current-source function of the driver 38, the meter 50 also provides an indication of the magnitude of the current flow in the coils 32 of the transducer 30. The intensity of the magnetic fields produced by the current in the coils 32 is proportional to the magnitude of the current and, accordingly, the reading of the meter 50 serves also as an indication of the intensity of the magnetic fields applied by the transducer 30 to the patient 34. The generator 40 is of well-known construction and provides a voltage with a periodic waveform. The generator 40 includes controls for selecting the AC frequency of the voltage, the waveform of the voltage, and the amplitude of the voltage. By way of example, the voltage may be a steady DC voltage, or may be varied in frequency over a range of 0.1 Hz to 10,000 Hz. The waveform may be sinusoidal, triangular, trapezoidal, square or a combination of more than one of these waveforms such as the sum of square plus sinusoid as shown in FIG. 8, by way of example.

The transducer 30 comprises a substrate 56 which supports the coils 32 in their respective positions in a two-dimensional array 58. By way of example in the practice of the invention, in one embodiment of transducer 30, the array 58 has a total of 16 of the coils 32 arranged in four rows, each of the rows having four of the coils 32, as shown in FIG. 5. Each coil 32 has, typically four or five turns, and has a diameter of approximately two centimeters, with an area of approximately three square centimeters. In a second embodiment of the transducer 30A, there is array 58A of the coils 32A having a total of 24 coils arranged in four rows each having six coils 32A, as shown in FIG. 5A. A cover layer 60 is disposed on top of the substrate 56 and the coils 32. The substrate 56 and the cover layer 60 are formed of a flexible electrically-insulating plastic material which permits flexing of the transducer 30 to conform to the curvature of the patient's head. The coils 32 are formed of a flexible electrically-conductive material such as copper which permits the foregoing flexing of the transducer 30.

In the case of energization of the coils 32 with a sinusoidal current, the generator 40 is operated to output a peak voltage, typically, of four volts relative to ground. This voltage provides a peak current of eight microamperes which is more than enough current to provide a peak magnetic field intensity of 60 picotesla. The output voltage of the generator 40 is adjusted to provide a desired intensity to the resultant alternating magnetic fields. If desired, the resistance of the resistor 42 may be reduced to provide still larger values of current for greater intensity of magnetic fields. Upon energization of the coils 32 with electric current, the resultant magnetic fields have lines of force parallel to the axes 62 of the respective coils 32. The locations of the coils 32 provide that the resultant magnetic fields are uniform. The driver 38 and the transducer 30 or 30A are capable of providing alternating magnetic fields in a frequency range of 0.1 Hz to 10 KHz, and intensity up to 60 microtesla. Typically, in the practice of the invention, the intensity of the alternating magnetic fields is in the range of 7.5–75 picotesla, and the frequency is in the range of 2 Hz–8 Hz.

Figure 9:
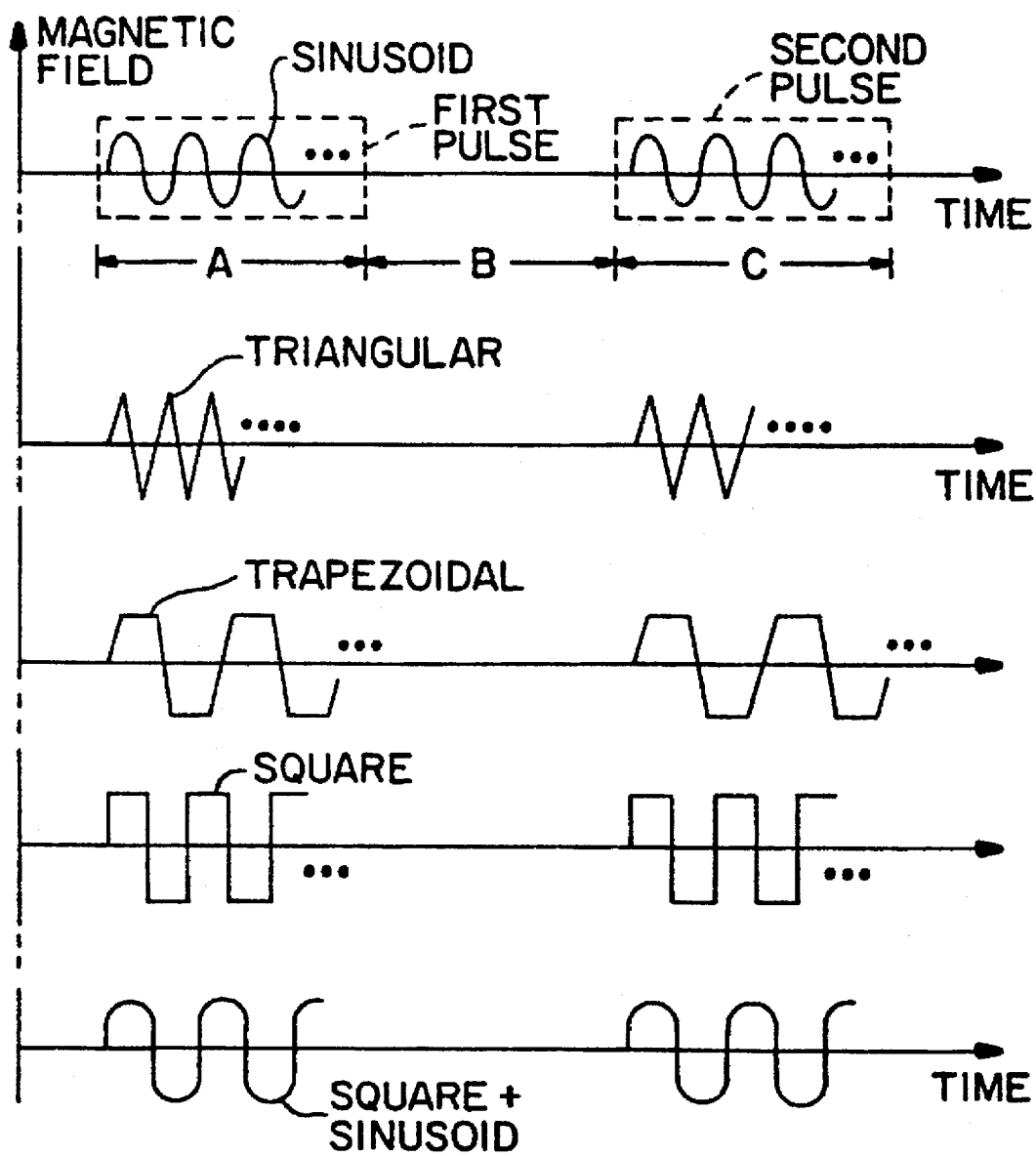
FIG. 9 is a diagram showing pulsation of the magnetic fields.

FIG. 9 shows a sequence of two pulses of magnetic fields wherein the direction and amplitude of the magnetic fields alternate in sinusoidal fashion. The sinusoidal form of the alternating magnetic fields is employed in the preferred embodiment of the invention. However, it is understood that some other waveform such as the aforementioned triangular or trapezoidal or square waveform may be used if desired. For example, in the case of the trapezoidal waveform, the rise and the fall times of the waveform together may occupy from 20% to 40% of each period of the waveform. Within each pulse, the AC frequency is held constant in the preferred embodiment of the invention. However, if desired, the AC frequency may be altered, as by a frequency ramp wherein the frequency increases during the pulse, such that the end frequency is greater than the initial frequency by 10%–30%.

FIG. 9 also shows the duration, A, of the first AC pulse, and the duration, B, of a rest interval or break between the AC pulses, and the duration, C, of the second AC pulse. The first AC pulse, for example, has a duration, A, of 15–20 minutes, the break, B, is in the range of 15–45 minutes, and the duration, C, of the second AC pulse is in the range of 15–45 minutes. The durations of the pulses are not critical; however, it has been noted that a duration of less than 5 minutes has virtually no effect on the patient's condition, while extending a pulse beyond 45 minutes provides no further improvement in the patient's condition. Generally, the duration of the second AC pulse exceeds the duration of the first AC pulse by 50%–100%. The intensity of the first AC pulse is equal to the intensity of the second AC pulse, in the preferred embodiment of the invention, the value of the intensity being in a range of approximately 7.5–75 picotesla. While the intensity of the magnetic fields may be varied from pulse to pulse, if desired, the intensity of the magnetic fields has been maintained constant in the practice of the method because no difference in clinical response of the patient has been noticed for different values of the magnetic fields within the foregoing range. A typical value for the intensity of the applied magnetic fields is 60 picotesla.

More specifically, in the case of a patient having Parkinson's disease, the second application is a combined AC/DC pulsed magnetic field of 15–45 minutes, C, while in the case of multiple sclerosis, the duration, C, which is a second AC pulsed magnetic field should be approximately 45 minutes. With respect to the AC frequency, in the case of multiple sclerosis, the first pulse frequency is 2 Hz–3 Hz and the second AC pulse frequency is 4 Hz–5 Hz, an increase of about 50%. For patients with Parkinson's disease, dystonia, tardive dyskinesia, Alzheimer's disease, migraine, depression, and schizophrenia the first pulse frequency is 5 Hz and the second pulse frequency is 8 Hz, also an increase of approximately 50%. For an epileptic patient, the first pulse frequency is 4 Hz and the second pulse frequency is 7 Hz, also an increase of approximately 50%. It is noted that the frequencies of stimulation employed for the multiple sclerosis patient tend to be in proximity to the delta brain wave activity (range of delta activity: 0.5 Hz–3 Hz) measured by an electroencephalogram (EEG), and that the frequencies employed for the patient with Parkinson's disease, dystonia, tardive dyskinesia, Alzheimer's disease, migraine, epilepsy, depression, and schizophrenia tend to be in proximity to the range of the theta brain wave activity (range of theta activity: 4 Hz–7 Hz).

The transmission of signals in the nervous system is such that within the neuron (nerve cell) transmission is accomplished by propagation of an electrical signal while between neurons signal propagation is accomplished via the mediation of a neurotransmitter. A neurotransmitter is a molecule, such as a molecule of serotonin, dopamine, acetylcholine, and histamine, or other neurotransmitter by way of example. During the propagation of an electrical signal the neurotransmitter is released from the transmitter neuron ("presynaptic neuron") into the synaptic cleft from which it diffuses across the synaptic cleft to reach specific receptors in the receiving neuron ("postsynaptic neuron"). Activation of these receptors at the postsynaptic neuron causes either excitation or inhibition of the postsynaptic neuron. The transmitter neuron and the receiving receptor at the postsynaptic neuron are specific to only one type of neurotransmitter so that a plurality of different forms of the neuron transmitter/receptor allow for transmission of different forms of signals by respective ones of the neurotransmitter.

Neurotransmitters are produced in numerous locations throughout the nervous system. For instance, serotonin is produced in neurons that originate in the median raphe of the brainstem and which project to numerous brain areas including the spinal cord, cerebellum, hypothalamus, limbic system, and cortex. In the central nervous system serotonin affects mood, sleep and arousal, satiety, emesis, cardiovascular regulation, temperature control, pain, sedation, anxiety and depression. In the peripheral nervous system, the primary actions of serotonin are on the gastrointestinal tract and cardiovascular system, but it also affects the respiratory tract and genito-urinary system.

It has been reported by patients who have been treated according to the present invention that they sense improvement in mood as well as motor and mental skills subsequent to the ingestion of the composition during the 4–8 week period preceding the initiation of magnetic treatment. These observations are in accordance with reports in the literature indicating that increased serotonin functions produces amelioration of symptoms of multiple sclerosis, Parkinson's disease, Alzheimer's disease, tardive dyskinesia, narcolepsy, depression including seasonal affective disorder and premenstrual syndrome (late luteal phase dysphoric disorder), migraine, schizophrenia, Gilles de la Tourette's syndrome, Attention Deficit-Hyperactivity Disorder, obsessive compulsive disorder, panic disorder, pain syndromes, narcolepsy, akathisia and restless legs syndrome, and myoclonus (Hyyppa el al., (1975) "Effect of L-tryptophan on central indoleamine metabolism and short-lasting neurologic disturbances in multiple sclerosis." *Journal of Neural Transmission*, 37, 297–304; Sano and Taniguchi (1972) "L-5-hydroxytryptophan (L-5-HTP) Therapie des Morbus Parkinson." *Munchen Medizinische Wochenschrift*, 114, 1717–1719; Meerwaldt (1986) "Treatment of hypokinetic rigid syndrome with fluvoxamine maleate." *Lancet*, 1, 977–978; Sandyk and Fisher (1989) "L-tryptophan supplementation in Parkinson's disease." *International Journal of Neuroscience*, 45, 215–219; McCance-Katz et al., (1992) "Serotonergic dysfunction in depression associated with Parkinson's disease." *Neurology*, 42, 1813–1814; Simpson and Foster (1986) "Improvement in organically disturbed behavior following trazodone treatment." *Journal of Clinical Psychiatry*, 47, 192–193; Pinner and Rich (1988) "Effects of trazodone on aggressive behavior in seven patients with organic mental disorders." *American Journal of Psychiatry*, 145, 1295–1296; Sandyk et al., (1986) "L-tryptophan in drug-induced movement disorders with insomnia." *New England Journal of Medicine*, 314, 1257; Sandyk et al., (1988) "Efficacy of L-tryptophan in neuroleptic-induced tardive dyskinesia." *Neurology*. (suppl 1), 38, 128; Kimball et al., (1960) "Effect of serotonin in migraine patients." *Neurology*, 10, 107–111; Asberg et al., (1986) "Therapeutic effects of serotonin uptake inhibitors in depression." *Journal of Clinical Psychiatry*, 46 (suppl. 4), (23–35); Levitt et al., (1991) "Tryptophan treatment and melatonin response in a patient with seasonal affective disorder." *Journal of Clinical Psychopharmacology*, 11, 74–75; Rickels et al., (1990) "Fluoxetine in the treatment of premenstrual syndrome." *Current Therapeutic Research*, 48, 161–166; Stone et al., (1991) "Fluoxetine in the treatment of late luteal phase dysphoric disorder" *Journal of Clinical Psychiatry*, 52, 290–293, Morand et al., (1983) "Clinical response of aggressive schizophrenics to oral tryptophan." *Biological Psychiatry*, 18, 575–577); Motplaisir and Godbout (1986) "Serotoninergic reuptake mechanisms in the control of cataplexy." *Sleep*, 9, 280–284; Frey and Darbonne (1994) "Fluoxetine suppresses human cataplexy: a pilot study." *Neurology*, 44, 707–709; Messiha and Carlson (1983) "Behavioral and clinical profiles of Tourette's syndrome. A comprehensive overview." *Brain Research Bulletin*, 11, 195–204; Van Woert and Chuang Hwang (1981) "Treatment of myoclonus." In A. Barbeau (Ed.), *Disorders of movement* (pp. 59–80). Lancaster, England: MTP Press; Gorman et al. (1989) "A neuroanatomical hypothesis for panic disorder." *American Journal of Psychiatry*, 146, 148–161; Sandyk (1985) "Efficacy of trazodone in narcolepsy." *European Neurology*, 24, 335–337; Sandyk et al. (1988) "L-tryptophan in neuroleptic-induced tardive dyskinesia." *International Journal of Neuroscience*, 42, 127–130; Sandyk (1990) "L-tryptophan in neuropsychiatric disorders: a review." *International Journal of Neuroscience*, 67, 127–144; Sandyk (1986) "L-tryptophan responsive restless legs syndrome." *American Journal of Psychiatry*, 143, 554–555; Sandyk and Fisher (1988) "Serotonin in involuntary movement disorders." *International Journal of Neuroscience*, 42, 185–205; Jenike et al. (1990)

"A controlled trial of fluvoxamine in obsessive-compulsive disorder: implications for a serotonergic theory." *American Journal of Psychiatry*, 147, 1209–1215; Thoren et al. (1980) "Clomipramine treatment of obsessive compulsive disorder. II. Biological aspects." *Archives of General Psychiatry*, 37, 1289–1294; Comings (1990) *"Tourette syndrome and human behavior."* (pp. 429–456), Duarte:CA: Hope Press).

Likewise, there have been also observations by patients of improvement in motor and mental functions upon receipt of only treatment with pulsed magnetic fields. However, the most dramatic improvements in motor functions and mental skills have been observed following treatment according to the present invention as described above.

With regard to the composition of the present invention, it is noted also that an increase of the concentration of serotonin in the brain cannot be accomplished by ingestion of the neurotransmitter serotonin since it does not pass from the blood into the brain (Wurtman and Fernstrom (1975) "Control of brain monoamine synthesis by diet and plasma amino acids." *The American Journal of Clinical Nutrition*, 28, 638–647). Therefore, any increase in the concentration of serotonin in the brain can be accomplished only by manufacture of serotonin within the brain. The amino-acid tryptophan or the immediate precursor of serotonin, 5-hydroxytryptophan (5-HTP), do cross from the blood into the brain. Therefore, L-tryptophan or L-5-HTP have been included in the composition, and are useful pharmacological strategies for elevation of brain's serotonin concentrations. Since in the pineal gland serotonin is converted to melatonin the administration of these serotonin precursors also enhances melatonin production.

The clinical response to the treatment is demonstrated by reference to FIGS. 1A–1C, 2A–2C and 3A–3D which are illustrative of successful treatments using the present method.

FIGS. 1A–C demonstrates the efficacy of externally applied AC magnetic fields in reversing the micrographia (small script) of a 69 year old patient having Parkinson's disease. For comparison purposes the drawings are presented without the use of the composition. FIG. 1A demonstrates the patient's drawing of a bicycle before magnetic treatment. Note the small size of the bicycle characteristic of the Parkinsonian micrographia. FIG. 1B shows the patient's drawing obtained 5 minutes after the application of the first pulsed magnetic treatment. Note the enlargement in the size of the bicycle. FIG. 1C shows the patient's drawing of the bicycle after 30 minutes of magnetic fields treatment composed of two 15-minute AC pulses of magnetic fields separated by a 15-minute break. Note the addition of details in the drawing as well as further enlargement of the size of the bicycle demonstrating reversal of the Parkinsonian micrographia.

The use of the foregoing procedure of administration of two 15-minute AC pulses of magnetic fields to give a total exposure of 30 minutes, wherein the two AC pulses are separated by a time interval in the range typically of 15 to 30 minutes, is employed also in the following examples.

Figure 2B:
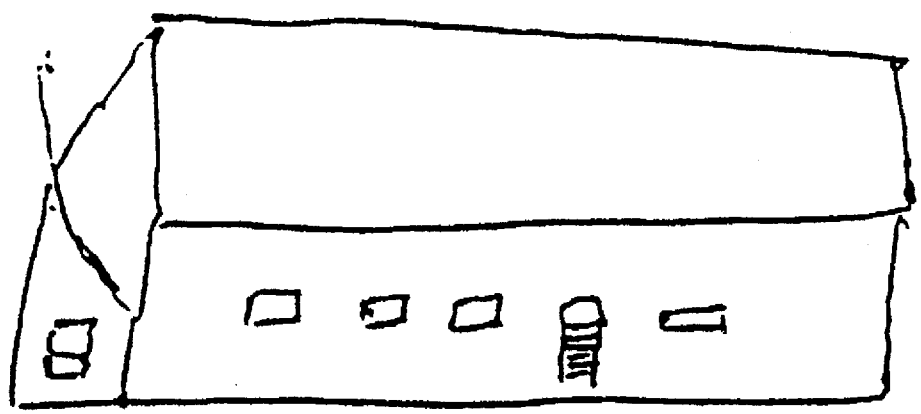

FIGS. 2A–C demonstrate the effect of pulsed magnetic fields on cognitive functions in a 70 year old male patient afflicted with Alzheimer's disease of five years duration. FIG. 2A shows the patient's drawing of a house before magnetic treatment. Note the simplicity of the design, a pattern which is frequently seen in patients with Alzheimer's disease (Kirk and Kertesz (1990) "On drawing impairment in Alzheimer's disease." *Archives of Neurology*, 48, 73–77). FIG. 2B shows the patient's performance after 30 minutes of magnetic treatment (15 minutes of first AC pulse—break of 20 minutes—15 minutes of second AC pulse). FIG. 2C shows the patient's performance after 30 minutes of magnetic treatment (first AC pulse 15 minutes—break 15 minutes—second AC pulse 15 minutes) which was administered in conjunction with the composition as described herein before.

Figure 3A:
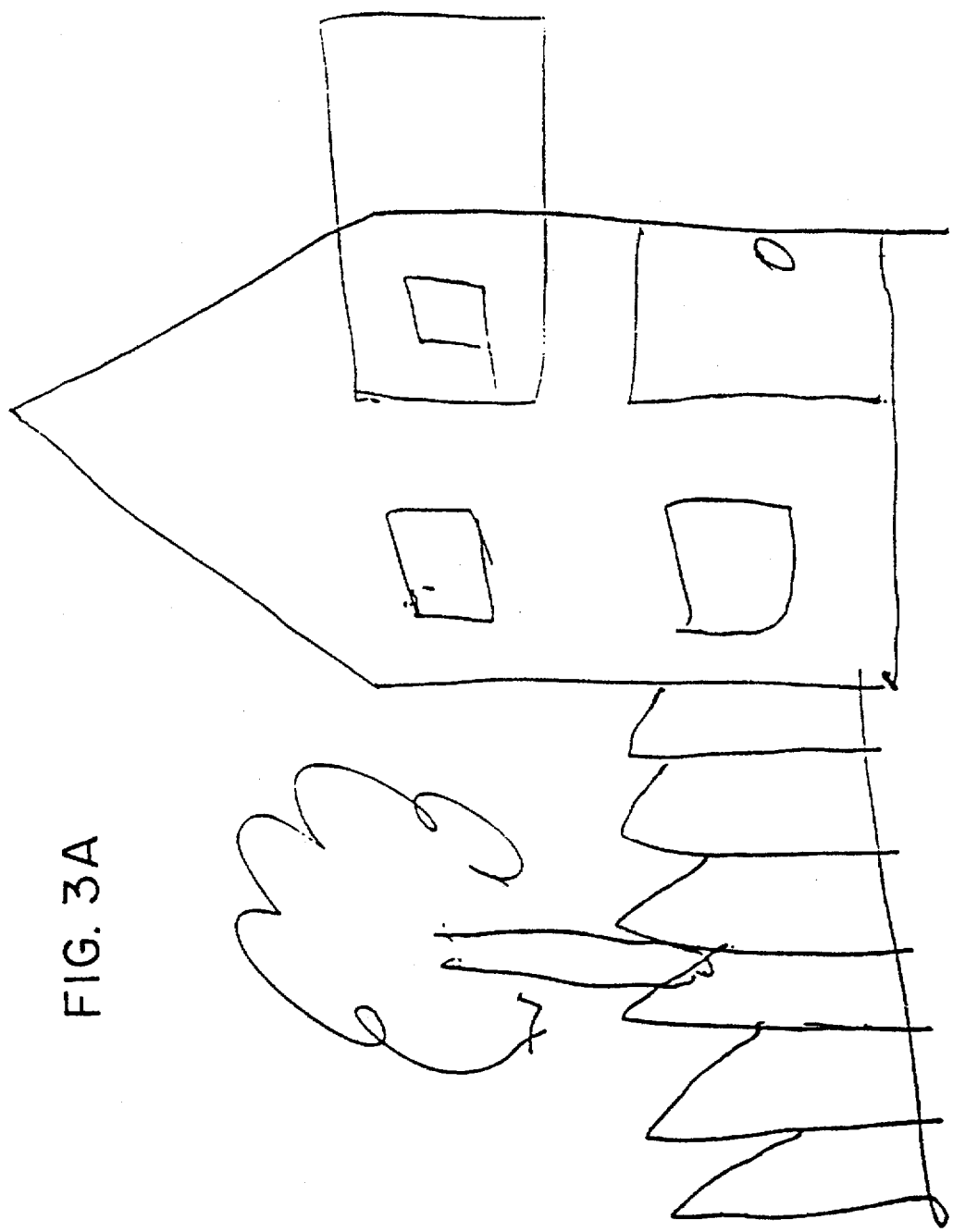
Figure 3B:
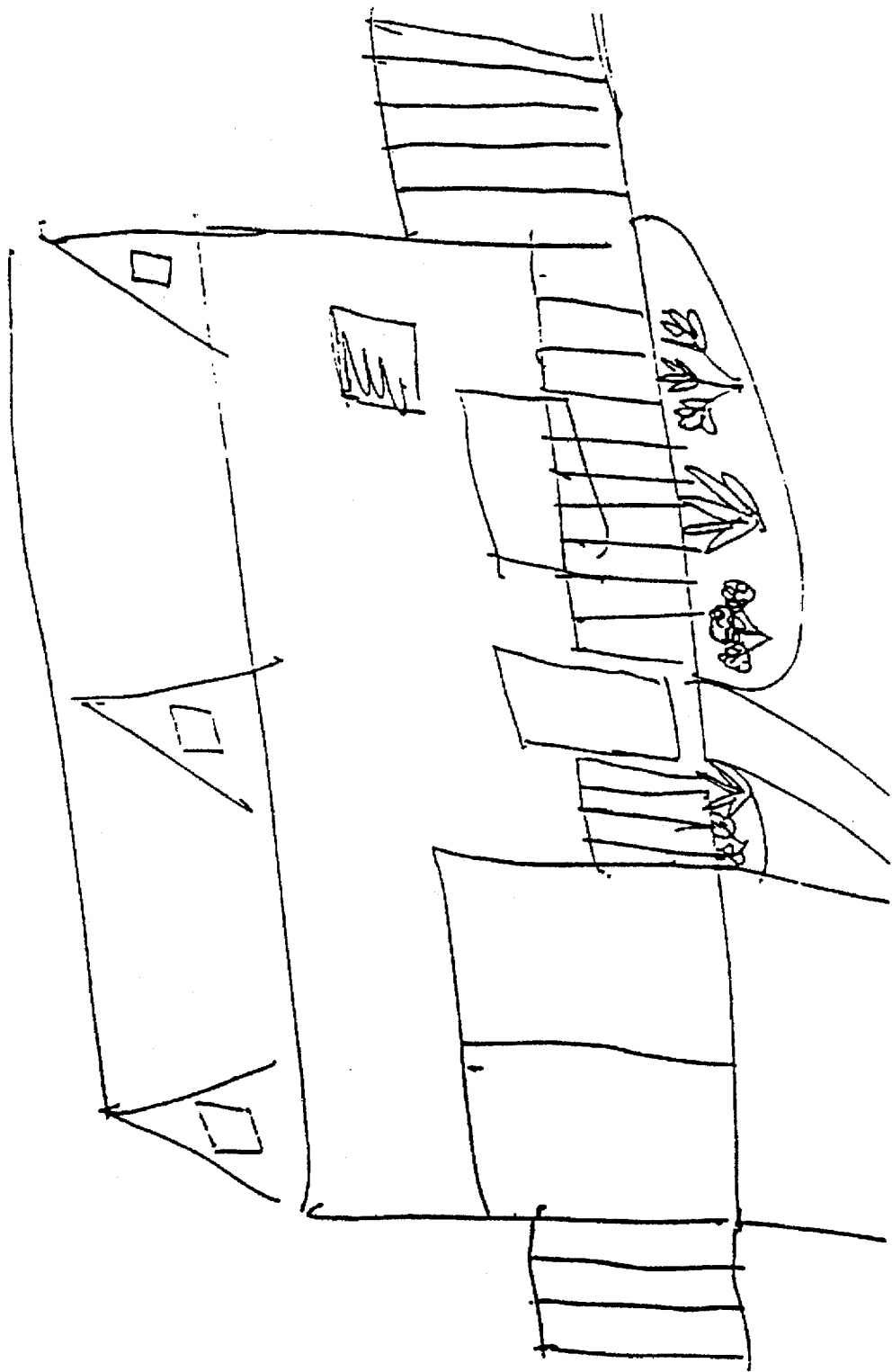
Figure 3C:
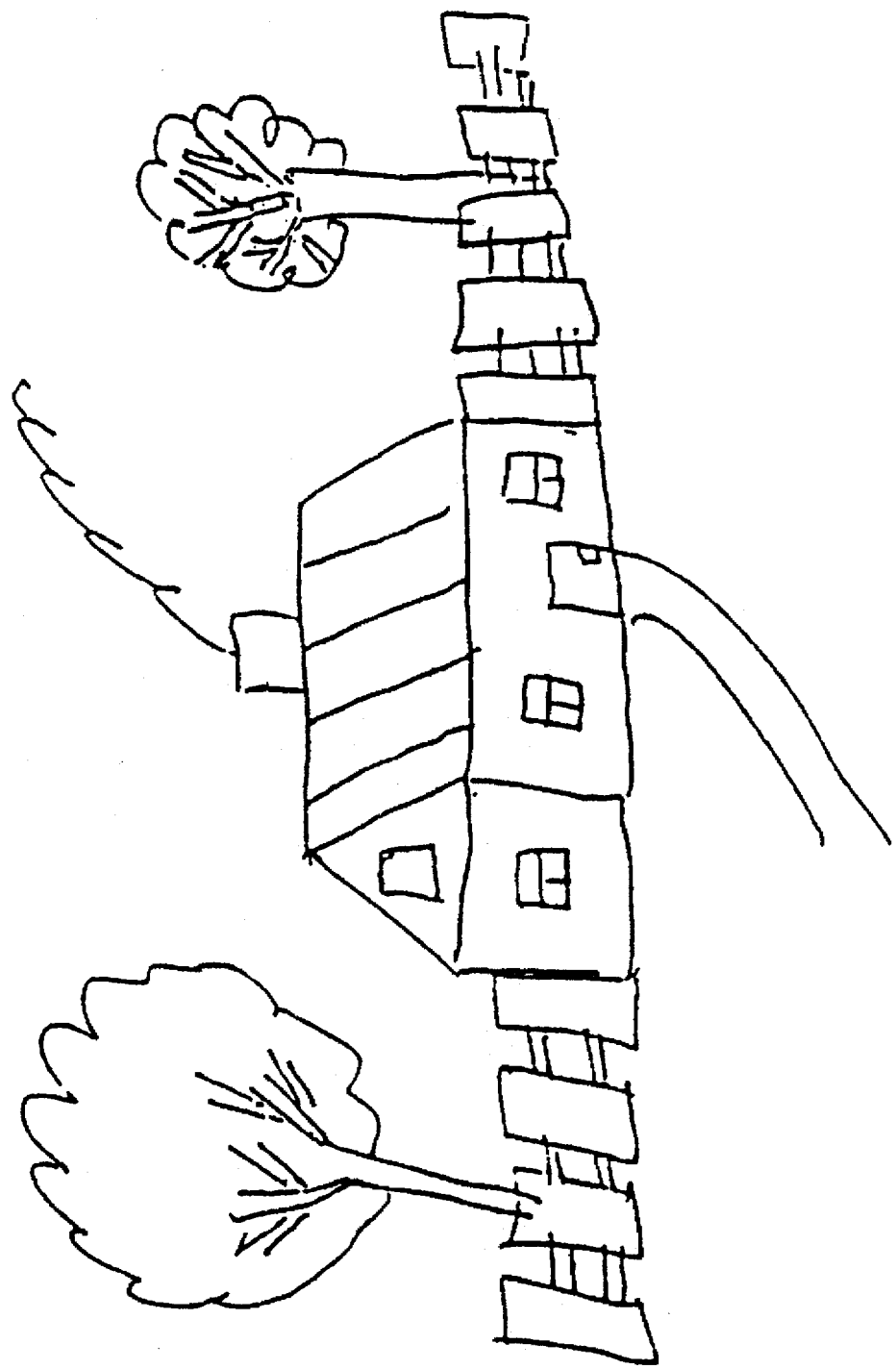
Figure 3D:
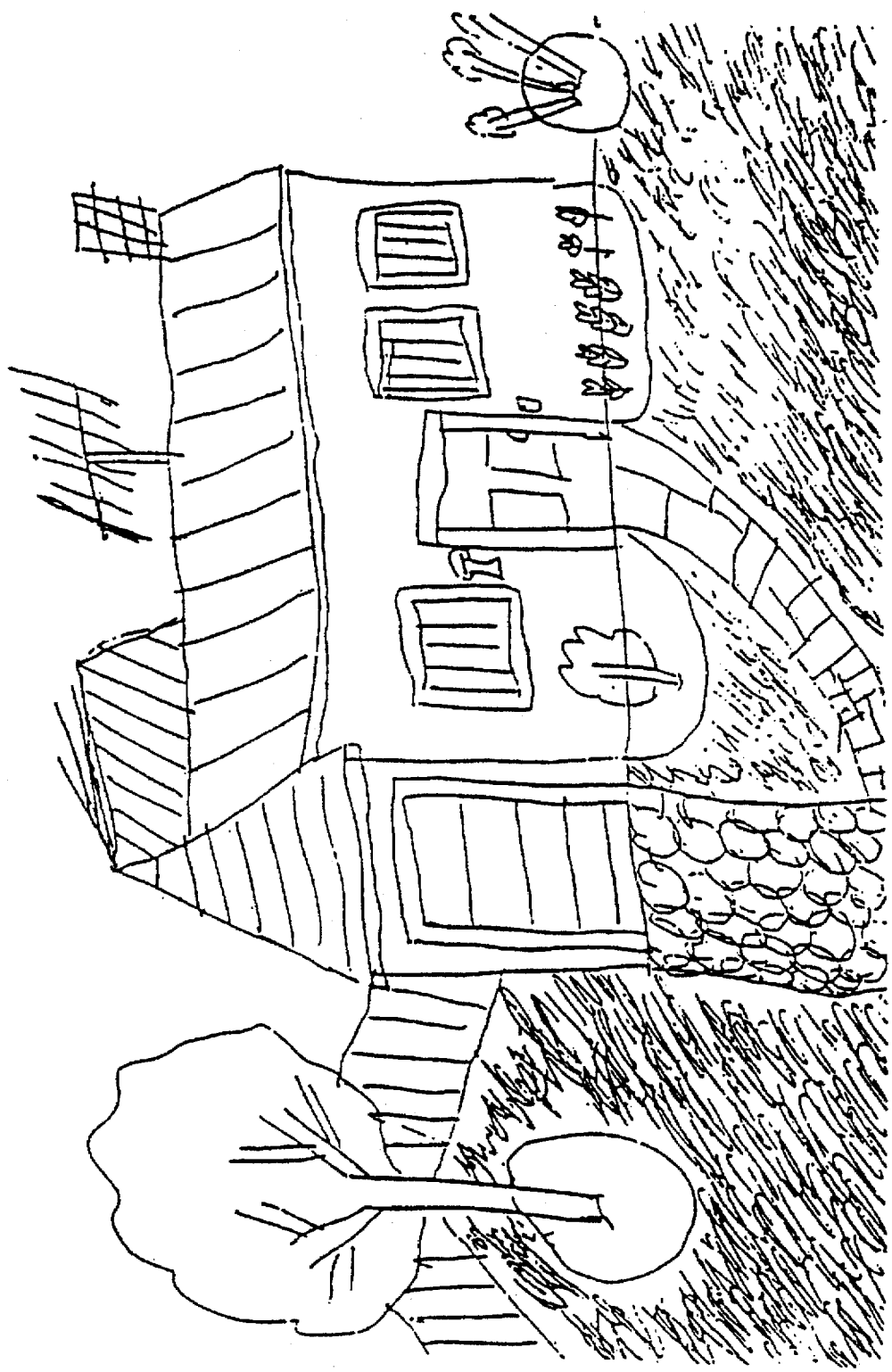

FIGS. 3A–D demonstrate the effect of the treatment according to the present invention on a 48 year old schizophrenic patient. FIG. 3A shows the patient's drawing of a house prior to the application of pulsed magnetic treatment. Note the simplicity of the design and poverty of perspectives. FIG. 3B shows the patient's drawing of a house after placebo treatment of 30 minutes. FIG. 3C shows the patient's drawing after application of pulsed magnetic treatment of 30 minutes duration (2 AC pulses of 15 minutes each). FIG. 3D shows the patient's performance when pulsed magnetic fields were applied in conjunction with the composition. Note the dramatic improvement in the perspectives of the drawing which included additional details.

Other and further uses and modifications of the method of the present invention will be more fully understood and appreciated by those skilled in the art by reference to the foregoing specification and the appended claims.

Figure 4A:

FIGS. 4A–C show attempts at a drawing by a 6½ year old child afflicted with Gilles de la Tourette's syndrome wherein FIG. 4A shows an attempted drawing of the human figure prior to magnetic treatment which showed distortions, lack of perspectives and details, and abnormal presentation of the hands each having three projections for fingers. FIG. 4B shows the child's drawing of the human figure after two 15 minute AC pulses of magnetic treatment. Note improvement in perceptual organization with improved perspectives. FIG. 4C shows the child's drawing after treatment according to the present invention which comprised administration of the composition of the present invention followed by the application of two fifteen minute AC pulses of magnetic fields according to the present invention. Note further improvement in the perspectives of the drawing and the addition of details including facial expression.

Other and further uses of my composition and method of treatment will be more fully appreciated by those skilled in fields.

What is claimed is:

1. A method of treating neurological and mental disorders which are associated with and related pathogenetically to deficient serotonin transmission and impaired pineal melatonin functions in humans and for treating neurological and mental disorders which are associated with or related pathogenetically to deficient serotonin neurotransfussion and impaired pineal melatonin functions in humans which comprises administering to a human in need thereof an effective amount of a composition which increases serotonin neurotransmission to the human to be treated followed by the application to the brain of the human of a sufficient amount of an AC pulsed magnetic field of proper intensity and frequency alone or in combination with a sufficient amount of a DC magnetic field of proper intensity and frequency to treat the disorder.

2. A method according to claim 1 which further comprises having the human consume a sufficient amount of a dietary composition which will increase plasma-tryptophan concentrations beginning prior to the application of the magnetic field.

3. A method according to claim 1 for the treatment of Gilles de la Tourette's syndrome wherein only the AC pulsed magnetic field is applied and the frequency is 2 Hz–7 Hz.

4. A method according to claim 1 for the treatment of Attention Deficit-Hyperactivity Disorder wherein only the AC pulsed magnetic field is applied and the frequency is 2 Hz–7 Hz.

5. A method according to claim 1 for the treatment of anxiety and panic disorder wherein only the AC pulsed magnetic field is applied and the frequency is 5 Hz–7 Hz.

6. A method according to claim 1 for the treatment of narcolepsy-cataplexy wherein only the AC pulsed magnetic field is applied and the frequency is 2 Hz–7 Hz.

7. A method according to claim 1 for the treatment of obsessive compulsive disorder wherein only the AC pulsed magnetic field is applied and the frequency is 5 Hz–8 Hz.

8. A method according to claim 1 for the treatment of akathisia and-restless legs syndrome wherein only the AC pulsed magnetic field is applied and the frequency is 5 Hz–8 Hz.

9. A method according to claim 1 for the treatment of myoclonus wherein only the AC pulsed magnetic field is applied and the frequency is 2 Hz.–7 Hz.

10. A method according to claim 1 for the treatment of chronic pain syndromes wherein only the AC pulsed magnetic field is applied and the frequency is 5 Hz–8 Hz.

11. A method according to claim 1 for the treatment of Parkinson's disease wherein both the AC pulsed magnetic field and the DC magnetic field are simultaneously applied.

12. A method according to claim 1 wherein the stimulant of serotonin receptors is an ergoloid mesylate, pergolide mesylate or buspirone.

13. A method according to claim 1 wherein the composition includes a stimulant of serotonin synthesis which is vitamin $B_1$, vitamin $B_3$, vitamin $B_6$, biotin, S-adenosylmethionine, folic acid, ascorbic acid, magnesium, coenzyme $Q_{10}$, piracetam, or mixtures of two or more thereof.

14. A method according to claim 13 wherein the composition includes the serotonin re-uptake inhibitor which is sertraline, nefazodone, trazodone or a mixture thereof.

15. A method according to claim 1 for the treatment of Parkinson's disease which comprises applying an AC pulsed magnetic field and a DC magnetic field of 5 Hz–8 Hz for 15–20 minutes, followed by a 15–45 minute interval, followed by applying an AC pulsed magnetic field and a DC magnetic field of 5 Hz–8 Hz for 15–45 minutes.

16. A method according to claim 15 wherein the AC pulsed magnetic field and the DC magnetic field are simultaneously applied together.

17. A method according to claim 2 wherein the dietary composition comprises tryptophan rich foods.

18. A method according to claim 17 wherein the tryptophan rich foods are turkey, milk, bananas, nuts and sunflower seeds.

19. A method according to claim 18 for the treatment of multiple sclerosis, depression, obsessive compulsive disorder, anxiety and panic disorder, Gilles de la Tourette's syndrome, and Alzheimer's disease and for the management of pain syndromes, wherein 4 oz. of turkey twice a week, 8 oz. of milk per day, 1 banana per day, 1–2 oz. of nuts per day and 3–4 oz. of sunflower sees per day are consumed by the human.

20. A method according to claim 1 wherein the magnetic fields are applied to the brain of the human using a helmet-like transducer array.

21. A method according to claim 20 wherein the helmet-like transducer array comprises an array of coils which are flat or helical.

22. The method according to claim 1, wherein the composition which increases serotonin transmission comprises an effective amount of a serotonin precursor, an effective amount of a stimulant to increase plasma tryptophan concentrations, an effective amount of a stimulant to facilitate the transport of tryptophan into the brain of the human, an effective amount of a stimulant of serotonin synthesis, an effective amount of a serotonin reuptake inhibitor, an effective amount of a stimulant of serotonin release and an effective amount of a stimulant of serotonin receptors.

23. The method according to claim 22, wherein the serotonin precursor is selected from the group consisting of L-tryptophan or L-5-hydroxytryptophan; the stimulant to increase plasma tryptophan concentrations is a salicylate; the stimulant to facilitate the transport of tryptophan into the brain is selected from the group consisting of vitamin $B_3$ and chromium; the stimulant of serotonin synthesis is selected from the group consisting of vitamin $B_1$, vitamin $B_3$, vitamin $B_6$, biotin, S-adenosylmethionine, folic acid, ascorbic acid, magnesium, coenzyme $Q_{10}$, and piracetam; the serotonin reuptake inhibitor is selected from the group consisting of sertraline, nefazodone, and trazodone; the stimulant of serotonin release is fenfluramine; and the stimulant of serotonin receptor is selected from the group consisting of ergoloid mesylate, pergolide mesylate, and buspirone.

* * * * *